(12) United States Patent
To et al.

(10) Patent No.: US 10,786,366 B2
(45) Date of Patent: *Sep. 29, 2020

(54) ANGLED, RIGID INTERVERTEBRAL SCAFFOLDING

(71) Applicant: INTEGRITY IMPLANTS INC., Palm Beach Gardens, FL (US)

(72) Inventors: John To, Newark, CA (US); John J. Flynn, Walnut Creek, CA (US); Paul J. Birkmeyer, Marshfield, MA (US)

(73) Assignee: INTEGRITY IMPLANTS INC., Palm Beach Gardens, FL (US)

(*) Notice: Subject to any disclaimer, the term of this patent is extended or adjusted under 35 U.S.C. 154(b) by 1 day.

This patent is subject to a terminal disclaimer.

(21) Appl. No.: 16/169,049

(22) Filed: Oct. 24, 2018

(65) Prior Publication Data
US 2019/0053913 A1 Feb. 21, 2019

Related U.S. Application Data

(63) Continuation of application No. 15/091,535, filed on Apr. 5, 2016, now Pat. No. 10,149,773, which is a
(Continued)

(51) Int. Cl.
*A61F 2/28* (2006.01)
*A61F 2/30* (2006.01)
(Continued)

(52) U.S. Cl.
CPC .............. *A61F 2/447* (2013.01); *A61F 2/442* (2013.01); *A61F 2/4611* (2013.01);
(Continued)

(58) Field of Classification Search
CPC ........ A61F 2/447; A61F 2/442; A61F 2/4611; A61F 2/30965; A61F 2/441;
(Continued)

(56) References Cited

U.S. PATENT DOCUMENTS 4,309,777 A  1/1982  Patil
4,733,665 A  3/1988  Palmaz
(Continued)

FOREIGN PATENT DOCUMENTS

CN  101909548  7/2014
EP  1011503  2/1998
(Continued)

OTHER PUBLICATIONS

U.S. Appl. No. 16/444,888, filed Dec. 13, 2012, To—owned by Applicant.
(Continued)

*Primary Examiner* — Pedro Philogene
(74) *Attorney, Agent, or Firm* — Brian S. Boyer; Syndicated Law, PC

(57) ABSTRACT

An intervertebral scaffolding system is provided having a central beam having a proximal portion having an end, a grafting portion having a top and a bottom, a distal portion having a end, a central beam axis, a graft distribution channel having an entry port at the end of the proximal portion, a top exit port at the top of the grafting portion, and a bottom exit port at the bottom of the grafting portion. These systems can also include a laterovertically-expanding frame operable for a reversible collapse from an expanded state into a collapsed state. The expanded state, for example, can be configured to have an open graft distribution window that at least substantially closes upon the reversible collapse.

20 Claims, 19 Drawing Sheets

Related U.S. Application Data continuation of application No. 14/157,504, filed on Jan. 16, 2014, now Pat. No. 9,333,092, which is a continuation of application No. 13/815,787, filed on Mar. 15, 2013, now Pat. No. 8,663,332.

(60) Provisional application No. 61/737,054, filed on Dec. 13, 2012.

(51) Int. Cl.
  *A61F 2/44* (2006.01)
  *A61F 2/46* (2006.01)

(52) U.S. Cl.
  CPC ........... *A61F 2/30965* (2013.01); *A61F 2/441* (2013.01); *A61F 2/4684* (2013.01); *A61F 2002/2817* (2013.01); *A61F 2002/2835* (2013.01); *A61F 2002/30019* (2013.01); *A61F 2002/30556* (2013.01); *A61F 2002/30579* (2013.01); *A61F 2002/30581* (2013.01); *A61F 2002/30593* (2013.01); *A61F 2002/30594* (2013.01); *A61F 2002/30777* (2013.01); *A61F 2002/30779* (2013.01); *A61F 2002/30785* (2013.01); *A61F 2002/444* (2013.01); *A61F 2002/4435* (2013.01); *A61F 2310/00011* (2013.01); *A61F 2310/00023* (2013.01); *A61F 2310/00029* (2013.01); *A61F 2310/00047* (2013.01); *A61F 2310/00053* (2013.01); *A61F 2310/00071* (2013.01); *A61F 2310/00179* (2013.01); *A61F 2310/00293* (2013.01)

(58) Field of Classification Search
  CPC ............ A61F 2/4684; A61F 2002/2817; A61F 2002/2835; A61F 2002/30019; A61F 2002/30556; A61F 2002/30579; A61F 2002/30581; A61F 2002/30593; A61F 2002/30594; A61F 2002/30777; A61F 2002/30779; A61F 2002/30785; A61F 2002/4435; A61F 2002/444; A61F 2310/00011; A61F 2310/00023; A61F 2310/00029; A61F 2310/00047; A61F 2310/00053; A61F 2310/00071; A61F 2310/00179; A61F 2310/00293
  USPC .................. 623/17.11–17.16; 606/246–279
  See application file for complete search history.

(56) References Cited

U.S. PATENT DOCUMENTS

| | | |
|---|---|---|
| 4,759,766 A | 7/1988 | Buettner-Janz et al. |
| 4,820,305 A | 4/1989 | Harms et al. |
| 4,997,432 A | 3/1991 | Keller |
| 5,192,327 A | 3/1993 | Brantigan |
| 5,221,261 A | 6/1993 | Termin et al. |
| 5,609,635 A | 3/1997 | Michelson |
| 5,658,336 A | 8/1997 | Pisharodi |
| 5,976,187 A | 11/1999 | Richelsoph |
| 5,980,522 A | 11/1999 | Koros |
| 5,980,552 A | 11/1999 | Pinchasik et al. |
| 6,039,761 A | 3/2000 | Li et al. |
| 6,102,950 A | 8/2000 | Vaccaro |
| 6,176,882 B1 | 1/2001 | Biedermann |
| 6,193,757 B1 | 2/2001 | Foley et al. |
| 6,368,351 B1 | 4/2002 | Glenn et al. |
| 6,375,682 B1 | 4/2002 | Fleischmann et al. |
| 6,395,031 B1 | 5/2002 | Foley et al. |
| 6,409,766 B1 | 6/2002 | Brett |
| 6,419,705 B1 | 7/2002 | Erickson |
| 6,432,107 B1 | 8/2002 | Ferree |
| 6,436,119 B1 | 8/2002 | Erb et al. |
| 6,443,989 B1 | 9/2002 | Jackson |
| 6,482,235 B1 | 11/2002 | Lambrecht et al. |
| 6,488,710 B2 | 12/2002 | Besselink |
| 6,575,899 B1 | 6/2003 | Foley et al. |
| 6,582,439 B1 | 6/2003 | Sproul |
| 6,582,441 B1 | 6/2003 | He et al. |
| 6,582,467 B1 | 6/2003 | Teitelbaum |
| 6,595,998 B2 | 7/2003 | Johnson et al. |
| 6,666,891 B2 | 12/2003 | Boehm, Jr. et al. |
| 6,821,276 B2 | 11/2004 | Lambrecht et al. |
| 6,821,298 B1 | 11/2004 | Jackson |
| 6,893,464 B2 | 5/2005 | Kiester |
| 7,018,415 B1 | 3/2006 | McKay |
| 7,083,650 B2 | 8/2006 | Moskowitz et al. |
| 7,087,055 B2 | 8/2006 | Lim et al. |
| 7,204,853 B2 | 4/2007 | Gordon et al. |
| 7,214,243 B2 | 5/2007 | Taylor |
| 7,217,293 B2 | 5/2007 | Branch |
| 7,544,208 B1 | 6/2009 | Mueller et al. |
| 7,621,950 B1 | 11/2009 | Globerman et al. |
| 7,643,884 B2 | 1/2010 | Pond et al. |
| 7,655,046 B2 | 2/2010 | Dryer et al. |
| 7,678,148 B2 | 3/2010 | Peterman |
| 7,731,751 B2 | 6/2010 | Butler et al. |
| 7,771,473 B2 | 8/2010 | Thramann |
| 7,819,921 B2 | 10/2010 | Grotz |
| 7,828,845 B2 | 11/2010 | Estes et al. |
| 7,828,849 B2 | 11/2010 | Lim |
| 7,846,206 B2 | 12/2010 | Oglaza et al. |
| 7,850,733 B2 | 12/2010 | Baynham et al. |
| 7,862,618 B2 | 1/2011 | White et al. |
| 7,879,098 B1 | 2/2011 | Simmons, Jr. |
| 7,909,872 B2 | 3/2011 | Zipnick |
| 7,918,888 B2 | 4/2011 | Hamada |
| 8,062,375 B2 | 11/2011 | Glerum et al. |
| 8,070,754 B2 | 12/2011 | Fabian et al. |
| 8,070,813 B2 | 12/2011 | Grotz et al. |
| 8,083,744 B2 | 12/2011 | Dorchak |
| 8,088,163 B1 | 1/2012 | Kleiner |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,123,810 B2 | 2/2012 | Gordon et al. |
| 8,167,950 B2 | 5/2012 | Aferzon et al. |
| 8,182,538 B2 | 5/2012 | O'Neil et al. |
| 8,187,332 B2 | 5/2012 | McLuen |
| 8,236,058 B2 | 8/2012 | Fabian et al. |
| 8,241,363 B2 | 8/2012 | Sommerich et al. |
| 8,267,939 B2 * | 9/2012 | Cipoletti ................. A61F 2/447 606/99 |
| 8,353,961 B2 | 1/2013 | McClintock |
| 8,353,963 B2 | 1/2013 | Glerum |
| 8,491,659 B2 | 7/2013 | Weiman et al. |
| 8,551,173 B2 * | 10/2013 | Lechmann .......... A61F 2/30771 623/17.12 |
| 8,628,578 B2 | 1/2014 | Miller et al. |
| 8,632,595 B2 | 1/2014 | Weiman |
| 8,663,332 B1 * | 3/2014 | To ........................ A61F 2/4611 623/17.16 |
| 8,845,731 B2 | 9/2014 | Weiman |
| 8,852,279 B2 | 10/2014 | Weiman et al. |
| 8,926,704 B2 | 1/2015 | Glerum et al. |
| 8,936,641 B2 * | 1/2015 | Cain .................... A61F 2/4611 623/17.16 |
| 8,940,048 B2 | 1/2015 | Butler et al. |
| 8,940,052 B2 | 1/2015 | Lechmann et al. |
| 9,060,876 B1 | 1/2015 | To |
| 8,986,387 B1 | 3/2015 | To |
| 9,034,041 B2 | 5/2015 | Wolters |
| 9,039,771 B2 | 5/2015 | Glerum et al. |
| 9,138,328 B2 | 9/2015 | Butler et al. |
| 9,186,259 B2 | 11/2015 | To |
| 9,216,095 B2 | 12/2015 | Glerum et al. |
| 9,278,008 B2 | 3/2016 | Perloff et al. |
| 9,320,610 B2 | 4/2016 | Alheidt et al. |
| 9,333,092 B2 * | 5/2016 | To ......................... A61F 2/442 |
| 9,351,848 B2 | 5/2016 | Glerum et al. |
| 9,402,733 B1 | 8/2016 | To |
| 9,402,739 B2 | 8/2016 | Weiman et al. |
| 9,445,918 B1 | 9/2016 | Lin et al. |

(56) References Cited

U.S. PATENT DOCUMENTS

| | | | |
|---|---|---|---|
| 9,463,052 B2 | 10/2016 | Geist | |
| 9,474,625 B2 | 10/2016 | Weiman | |
| 9,480,574 B2 | 11/2016 | Lee et al. | |
| 9,545,316 B2 | 1/2017 | Ashley et al. | |
| 9,561,116 B2 | 2/2017 | Weiman et al. | |
| 9,566,168 B2 | 2/2017 | Glerum et al. | |
| 9,655,744 B1 | 5/2017 | Pimenta | |
| 9,675,469 B2 | 6/2017 | Landry et al. | |
| 9,717,601 B2 | 8/2017 | Miller | |
| 9,737,411 B2 | 8/2017 | Loebl et al. | |
| 9,795,493 B1 | 10/2017 | Bannigan | |
| 9,801,640 B2 | 10/2017 | O'Neil et al. | |
| 9,801,733 B2 | 10/2017 | Wolters et al. | |
| 9,801,734 B1 | 10/2017 | Stein et al. | |
| 9,883,953 B1 | 2/2018 | To | |
| 9,889,019 B2 | 2/2018 | Rogers et al. | |
| 9,907,673 B2 | 3/2018 | Weiman et al. | |
| 9,913,727 B2 | 3/2018 | Thommen et al. | |
| 9,913,736 B2 | 3/2018 | To | |
| 9,987,143 B2 | 6/2018 | Robinson et al. | |
| 9,999,517 B2 | 6/2018 | To | |
| 10,058,350 B2 | 8/2018 | Geist | |
| 10,080,592 B2 | 9/2018 | Geist | |
| 10,085,849 B2 | 10/2018 | Weiman et al. | |
| 10,098,757 B2 | 10/2018 | Logan et al. | |
| 10,105,238 B2 | 10/2018 | Koch et al. | |
| 10,143,569 B2 | 12/2018 | Weiman et al. | |
| 10,149,773 B2 * | 12/2018 | To | A61F 2/447 |
| 10,154,911 B2 | 12/2018 | Predick et al. | |
| 10,322,014 B2 | 6/2019 | To | |
| 10,383,743 B2 | 8/2019 | To | |
| 2002/0040243 A1 | 4/2002 | Attali | |
| 2003/0074075 A1 | 4/2003 | Thomas et al. | |
| 2003/0083746 A1 | 5/2003 | Kuslich | |
| 2004/0010315 A1 | 1/2004 | Song | |
| 2004/0024463 A1 | 2/2004 | Thomas et al. | |
| 2005/0256576 A1 | 11/2005 | Moskowitz et al. | |
| 2006/0100706 A1 | 5/2006 | Shadduck | |
| 2006/0122701 A1 | 6/2006 | Kiester | |
| 2006/0167547 A1 | 7/2006 | Suddaby | |
| 2006/0287729 A1 | 12/2006 | Segal et al. | |
| 2007/0118222 A1 | 5/2007 | Lang | |
| 2007/0173939 A1 | 7/2007 | Kim et al. | |
| 2007/0219634 A1 | 9/2007 | Greenhalgh | |
| 2008/0009876 A1 | 1/2008 | Sankaran et al. | |
| 2008/0021556 A1 | 1/2008 | Edie | |
| 2008/0021559 A1 | 1/2008 | Thramann | |
| 2008/0147193 A1 | 6/2008 | Matthis | |
| 2008/0234687 A1 | 9/2008 | Schaller | |
| 2008/0281346 A1 | 11/2008 | Greenhalgh | |
| 2008/0281424 A1 | 11/2008 | Parry et al. | |
| 2009/0018524 A1 | 1/2009 | Greenhalgh | |
| 2009/0076607 A1 | 3/2009 | Aalsma et al. | |
| 2009/0138083 A1 | 5/2009 | Biyani | |
| 2009/0281551 A1 | 5/2009 | Frey | |
| 2009/0222043 A1 | 9/2009 | Altarac | |
| 2009/0234389 A1 | 9/2009 | Chuang | |
| 2010/0010542 A1 | 1/2010 | Jackson | |
| 2010/0010633 A1 | 1/2010 | Kohm | |
| 2010/0042218 A1 | 2/2010 | Nebosky et al. | |
| 2010/0198352 A1 | 8/2010 | Edie | |
| 2010/0217325 A1 | 8/2010 | Hochschuler | |
| 2010/0222884 A1 | 9/2010 | Greenhalgh | |
| 2010/0234956 A1 | 9/2010 | Attia | |
| 2010/0286783 A1 | 11/2010 | Lechmann et al. | |
| 2010/0292796 A1 | 11/2010 | Greenhalgh | |
| 2011/0022090 A1 | 1/2011 | Gordon | |
| 2011/0029082 A1 | 2/2011 | Hall | |
| 2011/0046748 A1 | 2/2011 | Martin | |
| 2011/0130835 A1 | 6/2011 | Ashley | |
| 2011/0172774 A1 | 7/2011 | Varela | |
| 2011/0190816 A1 | 8/2011 | Sheffer | |
| 2011/0282453 A1 | 11/2011 | Greenhalgh | |
| 2011/0301712 A1 | 12/2011 | Palmatier | |
| 2011/0319997 A1 | 12/2011 | Glerum | |
| 2012/0029636 A1 | 2/2012 | Ragab | |
| 2012/0035729 A1 | 2/2012 | Glerum et al. | |
| 2012/0046748 A1 | 2/2012 | Weiman | |
| 2012/0083889 A1 | 4/2012 | Purcell | |
| 2012/0089185 A1 | 4/2012 | Gabelberger | |
| 2012/0109319 A1 | 5/2012 | Perisic | |
| 2014/0039625 A1 | 7/2012 | To | |
| 2012/0209386 A1 | 8/2012 | Triplett et al. | |
| 2012/0271396 A1 | 10/2012 | Zheng | |
| 2012/0290090 A1 | 11/2012 | Glerum et al. | |
| 2012/0303126 A1 | 11/2012 | Kirschman | |
| 2013/0023996 A1 | 1/2013 | McCormack | |
| 2013/0184822 A1 | 7/2013 | Kleiner | |
| 2014/0243981 A1 | 8/2014 | Davenport et al. | |
| 2015/0100128 A1 | 4/2015 | Glerum et al. | |
| 2015/0190242 A1 | 7/2015 | Blain et al. | |
| 2015/0374508 A1 | 12/2015 | Sandul | |
| 2016/0015530 A1 | 1/2016 | To | |
| 2016/0256291 A1 | 9/2016 | Miller | |
| 2016/0317315 A1 | 11/2016 | Weiman | |
| 2016/0338854 A1 | 11/2016 | Serhan et al. | |
| 2017/0119540 A1 | 5/2017 | Greenhalgh | |
| 2017/0209282 A1 | 7/2017 | Aghayev et al. | |
| 2017/0224504 A1 | 8/2017 | Butler et al. | |
| 2017/0224505 A1 | 8/2017 | Butler et al. | |
| 2017/0231780 A1 | 8/2017 | D'urso | |
| 2017/0239063 A1 | 8/2017 | Predick | |
| 2017/0281358 A1 | 10/2017 | Wagner et al. | |
| 2017/0333198 A1 | 11/2017 | Robinson | |
| 2017/0333203 A1 | 11/2017 | Glerum et al. | |
| 2017/0354512 A1 | 12/2017 | Weiman et al. | |
| 2018/0042735 A1 | 2/2018 | Schell et al. | |
| 2018/0193164 A1 | 7/2018 | Shoshtaev | |
| 2018/0256357 A1 | 9/2018 | To | |
| 2018/0296361 A1 | 10/2018 | Butler et al. | |
| 2018/0360489 A1 | 12/2018 | Geist | |
| 2019/0060085 A1 | 2/2019 | Geist | |
| 2019/0117409 A1 | 4/2019 | Shoshtaev | |
| 2019/0209339 A1 | 7/2019 | To | |
| 2019/0254841 A1 | 8/2019 | To | |
| 2019/0269521 A1 | 9/2019 | Shoshtaev | |
| 2020/0046515 A1 * | 2/2020 | To | A61F 2/447 |

FOREIGN PATENT DOCUMENTS

| | | |
|---|---|---|
| EP | 1233732 | 2/2001 |
| EP | 2327377 | 3/2002 |
| EP | 1532949 | 11/2003 |
| EP | 2237748 | 1/2009 |
| JP | 2009/505686 | 7/2005 |
| WO | WO 1996/040015 | 6/1996 |
| WO | WO 2000/044319 | 1/2000 |
| WO | WO 2001/066047 | 7/2001 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | PCT/US2013/052799 | 7/2012 |
| WO | WO 2012/135764 | 10/2012 |
| WO | PCT/US2014/054437 | 2/2014 |
| WO | PCT/US2016/014100 | 12/2015 |
| WO | PCT/US2017/52708 | 9/2017 |
| WO | PCT/US2019/20354 | 3/2018 |
| WO | PCT/US2018/43517 | 7/2018 |

OTHER PUBLICATIONS

U.S. Appl. No. 16/527,294, filed Dec. 13, 2012, To—owned by Applicant.

U.S. Appl. No. 60/666,945 (priority for U.S. Pat. No. 7,731,751, cited herein), filed Mar. 31, 2005, Butler, et al.

U.S. Appl. No. 61/585,724 (priority for U.S. Pat. No. 9,463,052, cited herein), filed Jan. 12, 2012, Geist—owned by Applicant.

U.S. Appl. No. 61/737,054, filed Dec. 15, 2013, To—owned by Applicant.

(56) References Cited

OTHER PUBLICATIONS

U.S. Appl. No. 61/875,688 (priority for U.S. Pat No. 10/058,350, cited herein), filed Oct. 4, 2013, To—owned by Applicant.
U.S. Appl. No. 62/232,021 (priority for U.S. 2018/0193164, cited herein), filed Sep. 24, 2015, Geist—owned by Applicant.
U.S. Appl. No. 62/444,663 (priority for U.S. 2018/0193164, cited herein), filed Jan. 10, 2017, Shoshtaev—owned by Applicant.
U.S. Appl. No. 62/471,206 (priority for U.S. 2018/0193164, cited herein), filed Jan. 10, 2017, Shoshtaev—owned by Applicant.
U.S. Appl. No. 62/481,565 (priority for PCT/US2018/43517, cited herein), filed Jan. 10, 2017, Shoshtaev—owned by Applicant.
U.S. Appl. No. 62/536,335 (priority for PCT/US2018/43517, cited herein), filed Jul. 24, 2017, To—owned by Applicant.
U.S. Appl. No. 62/550,557 (priority for U.S. 16/113,040, cited herein), filed Aug. 25, 2017, Geist—owned by Applicant.
Written opinion and search report for PCT/US2013/052799, To—owned by Applicant, dated Dec. 2, 2012.
PCT/US2013/073435 Published as WO 2014/093136, To—owned by Applicant, Dec. 5, 2013.
Written opinion and search report for PCT/US2013/073435, To—owned by Applicant, dated Apr. 30, 2012.
Written opinion and search report for PCT/US2014/054437, To—owned by Applicant, dated Jan. 6, 2015.
Written opinion and search report for PCT/US2016/014100, To—owned by Applicant, dated Jan. 6, 2015.
Written opinion and search report for PCT/US2017/52708, To—owned by Applicant, dated Sep. 21, 2017.
PCT/US2016/053467 Published as WO 2017/053813, Geist—owned by Applicant, dated Sep. 24, 2015.
Written opinion and search report for PCT/US2016/053467, Geist—owned by Applicant, dated Sep. 24, 2015.
PCT/US2018/13207 Published as WO 2018/132502, Shoshtaev—owned by Applicant, dated Jan. 10, 2018.
Written opinion and search report for PCT/US2018/13207, Shoshtaev—owned by Applicant, dated Jan. 10, 2018.
Written opinion and search report for PCT/US2018/43517, To—owned by Applicant, dated Jul. 24, 2018.
Written opinion and search report for PCT/US2019/20354, Shoshtaev—owned by Applicant, dated Mar. 1, 2018.
European search report for EP 13862126, dated Dec. 5, 2013, To—owned by Applicant.
European search report for EP 14842880, dated Jun. 22, 2016, To—owned by Applicant.
European search report for EP 16740662, dated Nov. 29, 2017, To—owned by Applicant.
European search report for EP 19162909.6, dated Dec. 5, 2013, To—owned by Applicant.
Basho, R. et al. Lateral interbody fusion: Indications and techniques. Operative techniques in orthopaedics 21(3): 204-207 (Sep. 2011).
Caliber. www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
CAPSTONE® PEEK spinal system PLIF anf TLIF surgical technique. Medtronic Sofamor Danek 1-36 (2009).

COALIGN. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 ; [retrieved from the internet Nov. 16, 2017].
Interbody Fusion Cage (Neo IC) Source, www.tradekorea.com [online] URL: http://www.tradekorea.com/product-detail/P00015150/Interbody_Fusion_Cage_Neo_IC_.html [retrieved Feb. 13, 2013].
Kaech, D.L. et al. Spinal restabilization procedures, diagnostic and therapeutic aspects of intervertebral fusion cages, artificial discs and mobile implants. Elsevier Science B.V. Part II: 121-204(2002).
Kiapour, A. et al. A biomechanical finite element study of subsidence and migration tendencies in stand-alone fusion procedures—comparison of an in situ expandable device with a rigid device. J Spine 1(4): 5 pages (2012).
Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].
Powerbuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].
PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].
Sasani, M. et al. Single-stage posterior corpectomy and expandable cage placement for treatment of thoracic or lumbar burst fractures. Spine 34(1): E33-E40 (Jan. 1, 2009).
Spineology. OptiMesh 1500E deploying grafting system. [online] URL: http://www.spineology.com/fb/intl/products/products/optimesh 1500e.html (retrieved Jun. 3, 2013).
STAXX XD, www.spinewave.com. [online] URL: http://www.spinewave.com/products/xd_us.html [retrieved on Jan. 27, 2013].
SYNFIX-LR System. Instruments and implants for stand-alone anterior lumbar interbody fusion (ALIF). Synthes SynFix-LR system technique guide 52 pages. (2010).
Transforaminal Lumbar Interbody Fusion (TLIF). Virgina spine institute, Reston Virgina. [online] URL: http://www.spinemd.com/operative-treatments/tlif-transforaminal-lumbat-interbody-fusion.com 1-6 (2013). [retrieved on Jun. 16, 2013].
Uchida, K. et al. Anterior expandable strut cage replacement for osteoporotic thoracolumbar vertebral collapse. J Neurosurg Spine 4(6): 454-462 (Jun. 2006).
Xenos. Cage mesh system for spine. Biotek Chetan Meditech Pvt. Ltd. [online] URL: http://www.biotekortho.net/spine-treatment.html [retrieved on Feb. 13, 2013].
Zeus-O, [online] URL: http://www.amendia.com/zeuso.html [retrieved on Jan. 27, 2013].

\* cited by examiner

ANGLED, RIGID INTERVERTEBRAL SCAFFOLDING

CROSS-REFERENCE TO RELATED APPLICATIONS

This application is a continuation of Ser. No. 15/091,535, filed Apr. 5, 2016, which is a continuation of U.S. patent application Ser. No. 14/157,504, filed Jan. 16, 2014, now U.S. Pat. No. 9,333,092, which is a continuation of U.S. patent application Ser. No. 13/815,787, filed Mar. 15, 2013, now U.S. Pat. No. 8,663,332, which claims the benefit of U.S. Provisional Application No. 61/737,054, filed Dec. 13, 2012, each of which is hereby incorporated herein by reference in it's entirety.

BACKGROUND

Field of the Invention

The teachings herein are directed to a system for distributing bone graft material in an intervertebral disc space.

Description of the Related Art

Bone grafts are used in spinal fusion, for example, which is a technique used to stabilize the spinal bones, or vertebrae, and a goal is to create a solid bridge of bone between two or more vertebrae. The fusion process includes "arthrodesis", which can be thought of as the mending or welding together of two bones in a spinal joint space, much like a broken arm or leg healing in a cast. Spinal fusion may be recommended for a variety of conditions that might include, for example, a spondylolisthesis, a degenerative disc disease, a recurrent disc herniation, or perhaps to correct a prior surgery.

Bone graft material is introduced for fusion and a fusion cage can be inserted to help support the disc space during the fusion process. In fact, fusion cages are frequently used in such procedures to support and stabilize the disc space until bone graft unites the bone of the opposing vertebral endplates in the disc space. A transforaminal lumbar interbody fusion (TLIF), for example, involves placement of posterior instrumentation (screws and rods) into the spine, and the fusion cage loaded with bone graft can be inserted into the disc space. Bone graft material can be pre-packed in the disc space or packed after the cage is inserted. TLIF can be used to facilitate stability in the front and back parts of the lumbar spine promoting interbody fusion in the anterior portion of the spine. Fusion in this region can be beneficial, because the anterior interbody space includes an increased area for bone to heal, as well as to handle increased forces that are distributed through this area.

Unfortunately, therein lies a problem solved by the teachings provided herein. Currently available systems can be problematic in that the methods of introducing the fusion cage and bone graft material leaves pockets in regions of the intervertebral space that are not filled with bone graft material, regions in which fusion is desired for structural support. These pockets can create a premature failure of the fused intervertebral space due to forces that are distributed through the regions containing the pockets, for example, when the patient stands and walks.

Traditional fusion cages, such as the Medtronic CAPSTONE cage, are designed to be oversized relative to the disc space to distract the disc space as the entire cage is inserted. However, this makes it difficult to insert and position properly. In response to the problem, the art has developed a number of new fusion cages, such as the Globus CALIBER cage which can be inserted at a low height and expanded vertically to distract the disc space. Unfortunately, these types of devices have the typical graft distribution problem discussed above, in that they do not provide a path for bone graft to be inserted and fill in the space surrounding the cage or within the cage. They have other problems as well, including that the annulotomy must be large to accommodate a large enough cage for stability, and this large opening necessitates more trauma to the patient. Moreover, they can also create the additional problem of "backout", in that they cannot expand laterally beyond the annulotomy to increase the lateral footprint of the cage relative to lateral dimension of the annulotomy. Since it takes several months for the fusion to occur to completion in a patient, the devices have plenty of time to work their way out of the space through the large annulotomy.

Accordingly, and for at least the above reasons, those of skill in the art will appreciate bone graft distribution systems that facilitate an improved distribution of graft material throughout the intervertebral space. Such systems are provided herein, the systems configured to (i) effectively distribute bone graft material both from the system, and around the system, to improve the strength and integrity of a fusion; (ii) reduce or eliminate the problem of failures resulting from a poor bone graft distribution; (iii) have a small maximum dimension in a collapsed state for a low-profile insertion into the annulus in a minimally-invasive manner, whether using only a unilateral approach or a bilateral approach; (iv) laterally expand within the intervertebral space to avoid backout of the system through the annulotomy; (v) vertically expand for distraction of the intervertebral space; and, (vi) provide an expansion in the intervertebral space without contracting the system in length to maintain a large footprint and an anterior position adjacent to the inner, anterior annulus wall, distributing load over a larger area, anteriorly, against the endplates.

SUMMARY

The teachings herein are generally directed to a system for distributing bone graft material in an intervertebral disc space. The graft distribution systems can have, for example, a central beam having a proximal portion having an end, a grafting portion having a top and a bottom, a distal portion having a end, a central beam axis, a graft distribution channel having an entry port at the end of the proximal portion, a top exit port at the top of the grafting portion, and a bottom exit port at the bottom of the grafting portion. These systems can also include a laterovertically-expanding frame having a lumen, a first top beam, a second top beam, a first bottom beam, and a second bottom beam, each having a proximal portion and a distal portion, and each operably connected to each other at their respective proximal portions and distal portions with connector elements to form the laterovertically-expanding frame that is operable for a reversible collapse from an expanded state into a collapsed state. The expanded state, for example, can be configured to have an open graft distribution window that at least substantially closes upon the reversible collapse. In these embodiments, the laterovertically-expanding frame is adapted for receiving an insertion of the central beam to form the graft distribution system.

In some embodiments, the graft distribution systems can have a central beam with a central beam axis, a graft distribution channel with an entry port in fluid communication with a top exit port, and a bottom exit port. The central beam can also have a proximal portion having and end with the entry port, a grafting portion having the top exit port and the bottom exit port, and a distal portion. The central beam can also be sized to have a transverse cross-section having a maximum dimension ranging from 5 mm to 15 mm for placing the central beam into an intervertebral space through an annular opening having a maximum lateral dimension ranging from 5 mm to 15 mm, the intervertebral space having a top vertebral plate and a bottom vertebral plate. The central beam can also have a top surface with a first top-lateral surface and a second top-lateral surface, a bottom surface with a first bottom-lateral surface and a second bottom-lateral surface, a first side surface with a first top-side surface and a first bottom-side surface, and a second side surface with a second top-side surface and a second bottom-side surface.

The graft distribution system can also comprise a laterovertically-expanding frame configured for operably contacting the central beam to create a graft distribution system in vivo, the frame having a collapsed state with a transverse cross section having a maximum dimension ranging from 5 mm to 15 mm for placing the frame in the intervertebral space through the annular opening for expansion. Likewise, the frame can also have an expanded state with a transverse cross section having a maximum dimension ranging from 6.5 mm to 18 mm for retaining the frame in the intervertebral space, the expanded state operably contacting with the central beam in the intervertebral space. The frame can be defined as including a proximal portion having an end, a grafting portion, a distal portion having an end, and a central frame axis of the expanded state.

The frame can be configured to have a first top beam including a proximal portion having an end, a grafting portion, and a distal portion having an end, the first top beam configured for contacting the first top-lateral surface of the central beam and the first top-side surface of the central beam in the expanded state, the central axis of the first top beam at least substantially on (i) a top plane containing the central axis of the first top beam and the central axis of a second top beam and (ii) a first side plane containing the central axis of the first top beam and the central axis of a first bottom beam. Likewise, the frame can be configured to have a second top beam including a proximal portion having an end, a grafting portion having an end, and a distal portion (not shown) having an end, the second top beam configured for contacting the second top-lateral surface of the central beam and the second top-side surface of the central beam in the expanded state, the central axis of the second top beam at least substantially on (i) the top plane and (ii) a second side plane containing the central axis of the second top beam and the central axis of a second bottom beam. Likewise, the frame can be configured to have a first bottom beam including a proximal portion having an end, a grafting portion, and a distal portion having an end, the first bottom beam configured for contacting the first bottom-lateral surface of the central beam and the first bottom-side surface of the central beam in the expanded state, the central axis of the first bottom beam at least substantially on (i) a bottom plane containing the central axis of the first bottom beam and the central axis of a second top beam and (ii) the first side plane. Likewise, the frame can be configured to have a second bottom beam including a proximal portion having an end, a grafting portion having an end, and a distal region having an end, the second bottom beam configured for contacting the second bottom-lateral surface of the central beam and the second bottom-side surface of the central beam in the expanded state, the central axis of the second bottom beam being at least substantially on (i) the bottom plane and (ii) a second side plane containing the central axis of the second bottom beam and the second top beam.

The beams of the laterovertically-expanding frame can be operably connected through connector elements. As such, the frame can include a plurality of proximal top connector elements configured to expandably connect the proximal portion of the first top beam to the proximal portion of the second top beam, the expanding consisting of a flexing at least substantially on a top plane containing the central axis of the first top beam and the central axis of the second top beam. Likewise the frame can be configured to have a plurality of distal top connector elements configured to expandably connect the distal portion of the first top beam to the distal portion of the second top beam, the expanding consisting of a flexing at least substantially on the top plane.

Likewise, the frame can be configured to have a plurality of proximal bottom connector elements configured to expandably connect the proximal portion of the first bottom beam to the proximal portion of the second bottom beam, the expanding consisting of a flexing at least substantially on a bottom plane containing the central axis of the first bottom beam and the central axis of the second bottom beam. Likewise, the frame can be configured to have a plurality of distal bottom connector elements configured to expandably connect the distal portion of the first bottom beam to the distal portion of the second bottom beam, the expanding consisting of a flexing at least substantially on the bottom plane.

Likewise, the frame can be configured to have a plurality of proximal first side connector elements configured to expandably connect the proximal portion of the first top beam to the proximal portion of the first bottom beam, the expanding consisting of a flexing at least substantially on a first side plane containing the central axis of the first top beam and the central axis of the first bottom beam; a plurality of distal first side connector elements (not shown) configured to expandably connect the distal portion of the first top beam to the distal portion of the first bottom beam, the expanding consisting of a flexing at least substantially on the first side plane. Likewise the frame can be configured to have a plurality of proximal second side connector elements configured to expandably connect the proximal portion of the second top beam to the proximal portion of the second bottom beam, the expanding consisting of a flexing at least substantially on a second side plane containing the central axis of the second top beam and the central axis of the second bottom beam; a plurality of distal second side connector elements configured to expandably connect the distal portion of the second top beam to the distal portion of the second bottom beam, the expanding consisting of a flexing at least substantially on the second side plane;

The frame can be configured for slidably engaging with the central beam in vivo following placement of the central beam in the intervertebral space through the annular opening, the slidably engaging including translating the central beam into the frame from the proximal end of the frame toward the distal end of the frame in vivo; the translating including keeping the central beam axis at least substantially coincident with the central frame axis during the translating to create the graft distribution system in vivo through the annular opening. The graft distribution system can also be configured to form a top graft-slab depth between the top surface of the central beam and the top vertebral endplate; and, a bottom graft-slab depth between the bottom surface of the central beam and the bottom vertebral endplate in vivo. And, in some embodiments, the transverse cross-section of the graft distribution system in vivo is greater than the maximum lateral dimension of the annular opening to avoid backout.

The distal end of the frame can be configured to have a laterovertically operable connection with a guide plate connectable to the guidewire that restricts the first top beam, the first bottom beam, the second top beam, and the second bottom beam to laterovertical movement relative to the guide plate and the guidewire when converting the frame from the collapsed state to the expanded state in vivo. And, in some embodiments, the laterovertically-expandable frame has a lumen, and the guide plate has a luminal side with connector for reversibly receiving a guide wire for inserting the laterovertically-expandable frame into the intervertebral space.

One of skill will appreciate that the central beam can have any configuration that would be operable with the teachings provided herein. In some embodiments, criteria for a suitable central beam may include a combination of a material and configuration that provides a suitable stiffness. In some embodiments, the central beam can comprise an I-beam.

One of skill will further appreciate that the central beam can have any one or any combination of graft port configurations that would be operable with the teachings provided herein. In some embodiments, criteria for a suitable graft port configuration may include a combination of port size, number of ports, and placement of ports. In some embodiments, the central beam can comprise a side graft port.

One of skill will further appreciate that the connector elements can vary in design but should meet the constraints as taught herein. In some embodiments, for example each of the connector elements can have a cross-sectional aspect ratio of longitudinal thickness to transverse thickness ranging from 1:2 to 1:8.

In some embodiments, each of the plurality of proximal connector elements are proximal struts configured in an at least substantially parallel alignment in the expanded state; and, each of the distal connector elements are distal struts configured in an at least substantially parallel alignment in the expanded state. Likewise, in some embodiments, each of the plurality of proximal connector elements are proximal struts configured in an at least substantially parallel alignment in the collapsed state; and, each of the distal connector elements are distal struts configured in an at least substantially parallel alignment in the collapsed state. Moreover, in some embodiments, each of the plurality of proximal connector elements are proximal struts configured in an at least substantially parallel alignment in the expanded state and the collapsed state; and, each of the distal connector elements are distal struts configured in an at least substantially parallel alignment in the expanded state and the collapsed state.

In some embodiments, each plurality of proximal top connector elements and proximal bottom connector elements are proximal struts configured in an at least substantially parallel alignment in the expanded state and the collapsed state; and, each plurality of distal top connector elements and distal bottom connector elements are distal struts configured in an at least substantially parallel alignment in the expanded state and the collapsed state. In some embodiments, the proximal top struts are configured monolithically integral to the first top beam and the second top beam and adapted to flex toward the distal top struts during collapse; and, the distal top struts are configured monolithically integral to the first top beam and the second top beam and adapted to flex toward the proximal top struts during collapse. Likewise, in some embodiments, the proximal bottom struts are configured monolithically integral to the first bottom beam and the second bottom beam and adapted to flex toward the distal bottom struts during collapse; and, the distal bottom struts are configured monolithically integral to the first bottom beam and the second bottom beam and adapted to flex toward the proximal bottom struts during collapse. And, in these embodiments, the top and bottom of the laterovertically-expanding frame are each configured to open a graft distribution window upon expansion to facilitate graft distribution within the intervertebral space.

In some embodiments, the central beam further comprises a first side graft port and a second side graft port. In these embodiments, each plurality of proximal connector elements can be configured as proximal struts in an at least substantially parallel alignment in the expanded state and the collapsed state; and, each plurality distal connector elements are distal struts can be configured in an at least substantially parallel alignment in the expanded state and the collapsed state. As such, the proximal top struts can be configured monolithically integral to the first top beam and the second top beam and adapted to flex toward the distal top struts during collapse; and, the distal top struts can be configured monolithically integral to the first top beam and the second top beam and adapted to flex toward the proximal top struts during collapse. Likewise, the proximal bottom struts can be configured monolithically integral to the first bottom beam and the second bottom beam and adapted to flex toward the distal bottom struts during collapse; and, the distal bottom struts can be configured monolithically integral to the first bottom beam and the second bottom beam and adapted to flex toward the proximal bottom struts during collapse. Likewise, the proximal first side struts can be configured monolithically integral to the first top beam and the first bottom beam and adapted to flex toward the distal first side struts during collapse; and, the distal first side struts can be configured monolithically integral to the first top beam and the first bottom beam and adapted to flex toward the proximal first side struts during collapse. Likewise, the proximal second side struts can be configured monolithically integral to the second top beam and the second bottom beam and adapted to flex toward the distal second side struts during collapse; and, the distal second side struts can be configured monolithically integral to the second top beam and the second bottom beam and adapted to flex toward the proximal second side struts during collapse. As such, in some embodiments, the top, bottom, first side, and second side of the laterovertically-expanding frame can be configured to form a monolithically integral frame, each adapted to open a graft distribution window 188 upon expansion to facilitate graft distribution within the intervertebral space.

The teachings are also directed to a method of fusing an intervertebral space using any of the graft distribution systems taught herein. The methods can include creating a single point of entry into an intervertebral disc, the intervertebral disc having a nucleus pulposus surrounded by an annulus fibrosis, and the single point of entry having the maximum lateral dimension created through the annulus fibrosis. The methods can also include removing the nucleus pulposus from within the intervertebral disc through the single point of entry, leaving the intervertebral space for expansion of the graft distribution system within the annulus fibrosis, the intervertebral space having the top vertebral plate and the bottom vertebral plate. The methods can also include inserting the laterovertically expanding frame in the collapsed state through the single point of entry into the intervertebral space; and, inserting the central beam into the frame to form the graft distribution system. Moreover, the methods can also include adding a grafting material to the intervertebral space through the entry port.

The bone graft distribution systems provided herein include bone graft windows defined by the connector elements, the bone graft windows opening upon expansion of the laterovertically expanding frame. In some embodiments, the method further comprises opening a bone graft window, wherein the connector elements include v-shaped struts that (i) stack either proximally or distally in a closed-complementary configuration in the collapsed state to minimize void space for a low profile entry of the system both vertically and laterally into the intervertebral space, and (ii) deflect upon expansion to open the bone graft window.

The bone graft distribution systems provided herein also allow for independent expansion laterally and vertically by expanding in steps. In some embodiments, the expanding includes selecting an amount of lateral expansion independent of an amount of vertical expansion. And, in some embodiments, the lateral expansion exceeds the width of the annular opening that is the single point of entry into the intervertebral space. For example, the lateral dimension of the single point of entry can range from about 5 mm to about 15 mm in some embodiments. As such, in some embodiments, the expanding includes expanding the laterovertically expanding frame laterally to a width that exceeds the width of the single point of entry; and, inserting the central beam to expand the laterovertically expanding frame vertically to create the graft distribution system.

The bone graft distribution systems provided herein also have means for retaining the central beam in the laterovertically expanding frame. In some embodiments, the inserting of the central beam into the laterovertically expanding frame includes engaging a ratchet mechanism comprising a protuberance on the central beam that engages with the laterovertically-expanding frame to prevent the central beam from backing out of the laterovertically-expanding frame after the expanding.

The bone graft distribution systems provided here can be in the form of a kit. The kits can include, for example, a graft distribution system taught herein, a cannula for inserting the graft distribution system into the intervertebral space, a guidewire adapted for guiding the central beam into the laterovertically expanding frame, and an expansion handle for inserting the central beam into the laterovertically expanding frame to form the graft distribution system.

DETAILED DESCRIPTION OF THE INVENTION

Figure 1A:
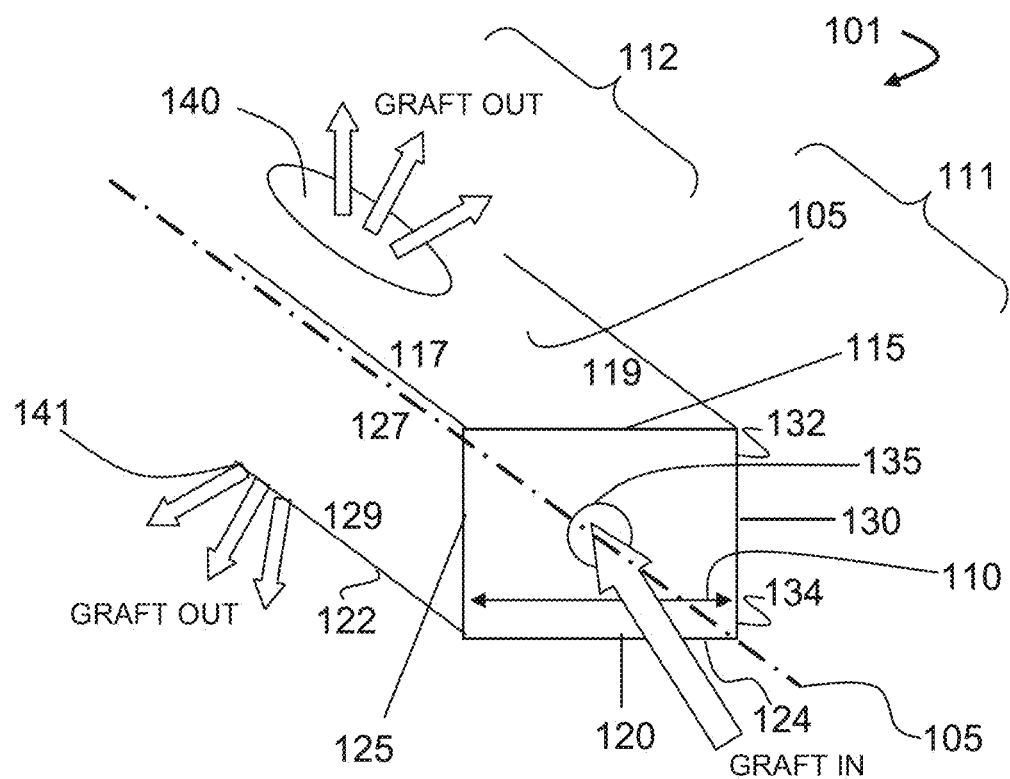
FIGS. 1A-1I illustrate components of the graft distribution system, according to some embodiments.

The teachings herein are generally directed to a system for distributing bone graft material in an intervertebral disc space. The graft distribution systems can have, for example, a central beam having a proximal portion having an end, a grafting portion having a top and a bottom, a distal portion having a end, a central beam axis, a graft distribution channel having an entry port at the end of the proximal portion, a top exit port at the top of the grafting portion, and a bottom exit port at the bottom of the grafting portion. These systems can also include a laterovertically-expanding frame having a lumen, a first top beam, a second top beam, a first bottom beam, and a second bottom beam, each having a proximal portion and a distal portion, and each operably connected to each other at their respective proximal portions and distal portions with connector elements to form the laterovertically-expanding frame that is operable for a reversible collapse from an expanded state into a collapsed state. The expanded state, for example, can be configured to have an open graft distribution window that at least substantially closes upon the reversible collapse. In these embodiments, the laterovertically-expanding frame is adapted for receiving an insertion of the central beam to form the graft distribution system.

In some embodiments, the graft distribution systems can also include a laterovertically-expanding frame having a first top beam, a second top beam, a first bottom beam, and a second bottom beam; wherein, the beams are in an at least substantially parallel arrangement with each other, each having a proximal portion, a grafting portion, and a distal portion, and each operably connected to each other at their respective proximal portions and distal portions to form the laterovertically-expanding frame in a square, cylindrical shape that is operable for a reversible collapse from an expanded state into a collapsed state. The expanded state, for example, can be configured to have an open graft distribution window that at least substantially closes upon the reversible collapse. In these embodiments, the laterovertically-expanding frame is adapted for receiving an insertion of the central beam to form the graft distribution system.

The term "subject" and "patient" can be used interchangeably in some embodiments and refer to an animal such as a mammal including, but not limited to, non-primates such as, for example, a cow, pig, horse, cat, dog; and primates such as, for example, a monkey or a human. As such, the terms "subject" and "patient" can also be applied to non-human biologic applications including, but not limited to, veterinary, companion animals, commercial livestock, and the like. Moreover, terms of degree are used herein to provide relative relationships between the position and/or movements of components of the systems taught herein. For example, the phrase "at least substantially parallel" is used to refer to a position of one component relative to another. An axis that is at least substantially parallel to another axis refers to an orientation that is intended, for all practical purposes to be parallel, but it is understood that this is just a convenient reference and that there can be variations due to stresses internal to the system and imperfections in the devices and systems. Likewise, the phrase "at least substantially on a . . . plane" refers to an orientation or movement that is intended, for all practical purposes to be on or near the plane as a convenient measure of the orientation or movement, but it is understood that this is just a convenient reference and that there can be variations due to stresses internal to the system and imperfections in the devices and systems. Likewise, the phrase "at least substantially coincident" refers to an orientation or movement that is intended, for all practical purposes to be on or near, for example, an axis or a plane as a convenient measure of the orientation or movement, but it is understood that this is just a convenient reference and that there can be variations due to stresses internal to the system and imperfections in the devices and systems.

FIGS. 1A-1I illustrate components of the graft distribution system, according to some embodiments. As shown in FIG. 1A, the graft distribution systems 100 can have a central beam 101 with a central beam axis 105, a graft distribution channel with an entry port 135 in fluid communication with a top exit port 140, and a bottom exit port 141. The central beam 101 can also have a proximal portion 111 having and end with the entry port 135, a grafting portion 112 having the top exit port 140 and the bottom exit port 141, and a distal portion (not shown). The central beam 101 can also be sized to have a transverse cross-section 110 having a maximum dimension ranging from 5 mm to 15 mm for placing the central beam 101 into an intervertebral space through an annular opening having a maximum lateral dimension ranging from 5 mm to 15 mm, the intervertebral space having a top vertebral plate and a bottom vertebral plate. The central beam 101 can also have a top surface 115 with a first top-lateral surface 117 and a second top-lateral surface 119, a bottom surface 120 with a first bottom-lateral surface 122 and a second bottom-lateral surface 124, a first side surface 125 with a first top-side surface 127 and a first bottom-side surface 129, and a second side surface 130 with a second top-side surface 132 and a second bottom-side surface 134.

In some embodiments, the central beam can have transverse cross-sectional lateral dimension ranging from about 5 mm to about 15 mm. In some embodiments, the vertical dimension of the central beam can range from about 4 mm to about 12 mm, about 5 mm to about 11 mm, about 6 mm to about 10 mm, and about 7 mm to about 9 mm, about 6 mm to about 8 mm, about 6 mm, or any range or amount therein in increments of 1 mm. In some embodiments, the lateral dimension of the central beam can range from about 5 mm to about 15 mm, about 6 mm to about 14 mm, about 7 mm to about 13 mm, about 8 mm to about 12 mm, about 10 mm, or any range or amount therein in increments of 1 mm. In some embodiments, transverse cross-section of the central beam has an area with an effective diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein. In some embodiments, the width (mm)×height (mm) of the central beam can be 9.0×5.0, 9.0×6.0, 9.0×7.0, 9.0×8.0, 9.0×9.0, and 9.0×10.0, or any deviation in dimension therein in increments of +/−0.1 mm. And, in some embodiments, the central beam can have a transverse cross-sectional lateral or vertical dimension that ranges from 6.5 mm to 14.0 mm.

Figure 1B:
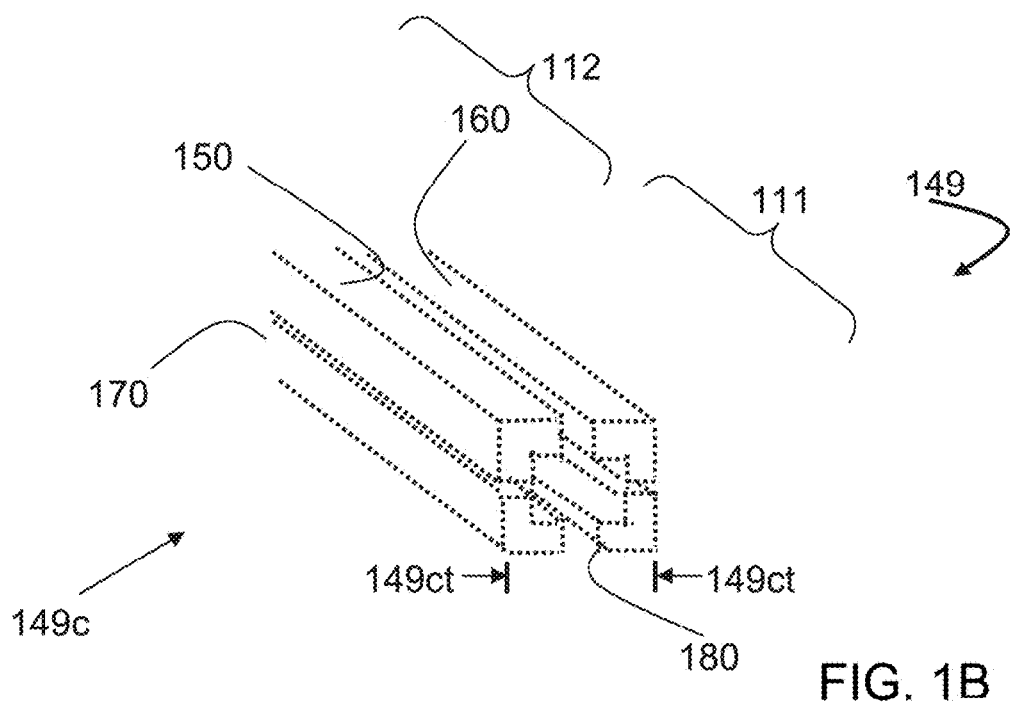
Figure 1C:
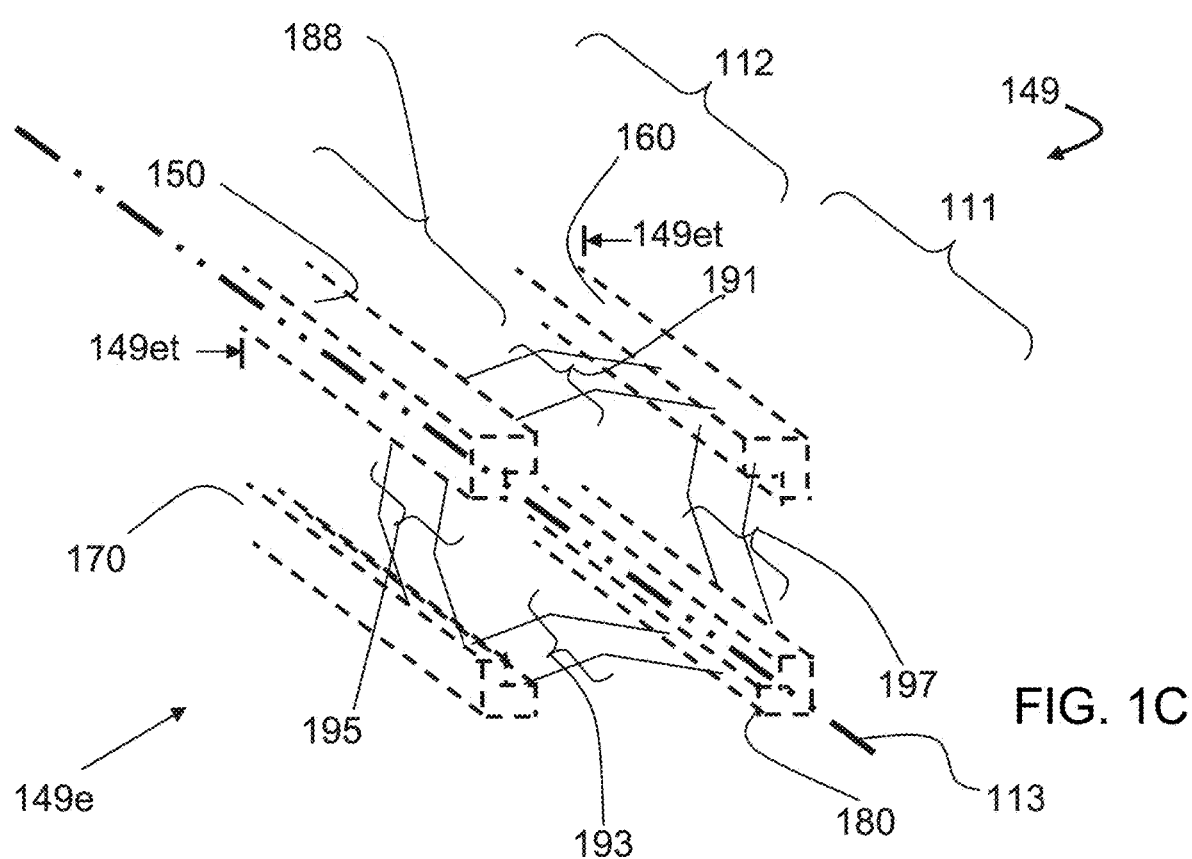

As shown in FIGS. 1B and 1C, the graft distribution system 100 can also comprise a laterovertically-expanding frame 149 configured for operably contacting the central beam 101 to create a graft distribution system 100 in vivo, the frame 149 having a collapsed state 149c with a transverse cross section 149ct having a maximum dimension ranging from 5 mm to 15 mm for placing the frame 149 in the intervertebral space through the annular opening for expansion. Likewise, the frame 149 can also have an expanded state 149e with a transverse cross section 149ct having a maximum dimension ranging from 6.5 mm to 18 mm for retaining the frame 149 in the intervertebral space, the expanded state operably contacting with the central beam 101 in the intervertebral space. The frame 149 can be defined as including a proximal portion 111 having an end, a grafting portion 112, a distal portion (not shown) having an end, and a central frame axis 113 of the expanded state 149e.

In some embodiments, the frame can have transverse cross-sectional lateral dimension in the collapsed state ranging from about 5 mm to about 15 mm. In some embodiments, the vertical dimension of the frame in the collapsed state can range from about 4 mm to about 12 mm, about 5 mm to about 11 mm, about 6 mm to about 10 mm, and about 7 mm to about 9 mm, about 6 mm to about 8 mm, about 6 mm, or any range or amount therein in increments of 1 mm. In some embodiments, the lateral dimension of the frame in the collapsed state can range from about 5 mm to about 15 mm, about 6 mm to about 14 mm, about 7 mm to about 13 mm, about 8 mm to about 12 mm, about 10 mm, or any range or amount therein in increments of 1 mm. In some embodiments, transverse cross-section of the frame in the collapsed state has an area with an effective diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein. In some embodiments, the width (mm)×height (mm) of the frame in the collapsed state can be 9.0×5.0, 9.0×6.0, 9.0×7.0, 9.0×8.0, 9.0×9.0, and 9.0×10.0, or any deviation in dimension therein in increments of +/−0.1 mm. In some embodiments, the frame can have a transverse cross-sectional dimension, lateral or vertical in the expanded state ranging from 4.0 mm to 18 mm, from 5.0 mm to 19.0 mm, from 6.0 mm to 17.5 mm, from 7.0 mm to 17.0 mm, from 8.0 mm to 16.5 mm, from 9.0 mm to 16.0 mm, from 9.0 mm to 15.5 mm, from 6.5 mm to 15.5 mm, or any range or amount therein in increments of +/−0.1 mm.

The term "collapsed state" can be used to refer to a configuration of the frame in which the transverse cross-sectional area, or profile, is at least substantially at it's minimum, and the term "expanded state" can be used to refer to a configuration of the frame that is expanded at least substantially beyond the collapsed state. In this context, a frame is expanded at least "substantially" beyond the collapsed state when a bone graft window of the frame has opened from the closed configuration by at least a 20% increase area of the bone graft window from the collapsed state. In some embodiments, the frame is expanded at least "substantially" beyond the collapsed state when a bone graft window of the frame has opened by at least a 15%, 20%, 25%, 30%, 35%, 40%, 45%, 50%, 60%, 70%, 80%, 90%, 100%, 150%, 200%, 250%, 300%, or more when compared to the bone graft window from the collapsed state. In some embodiments, the frame is expanded at least "substantially" beyond the collapsed state when a bone graft window of the frame has opened by at least 2×, 3×, 5×, 10×, 15×, 20×, or more when compared to the bone graft window from the collapsed state.

In some embodiments, the laterovertically expandable frames are created in an expanded state. And the expanded state can include a state that is at least 30%, at least 40%, at least 50%, at least 60%, at least 70%, at least 80%, at least 90%, or at least 95% of the full expansion. The term "full expansion" can be used to refer to an extent of expansion upon which a connector element begins to fatigue, fail, or crack; or, in some embodiments, strain beyond 10%, 20%, or 30%.

The frame 149 can be configured to have a first top beam 150 including a proximal portion 111 having an end, a grafting portion 112, and a distal portion (not shown) having an end, the first top beam 150 configured for contacting the first top-lateral surface 117 of the central beam and the first top-side surface 127 of the central beam 101 in the expanded state 149e, the central axis of the first top beam at least substantially on (i) a top plane containing the central axis of the first top beam and the central axis of a second top beam and (ii) a first side plane containing the central axis of the first top beam and the central axis of a first bottom beam. Likewise the frame 149 can be configured to have a second top beam 160 including a proximal portion 111 having an end, a grafting portion 112 having an end, and a distal portion (not shown) having an end, the second top beam 160 configured for contacting the second top-lateral surface 119 of the central beam 101 and the second top-side surface 132 of the central beam 101 in the expanded state 149e, the central axis of the second top beam at least substantially on (i) the top plane and (ii) a second side plane containing the central axis of the second top beam and the central axis of a second bottom beam. Likewise the frame 149 can be configured to have a first bottom beam 170 including a proximal portion 111 having an end, a grafting portion 112, and a distal portion (not shown) having an end, the first bottom beam 170 configured for contacting the first bottom-lateral surface 122 of the central beam 101 and the first bottom-side surface 129 of the central beam 101 in the expanded state 149e, the central axis of the first bottom beam at least substantially on (i) a bottom plane containing the central axis of the first bottom beam and the central axis of a second top beam and (ii) the first side plane. Likewise the frame 149 can be configured to have a second bottom beam 180 including a proximal portion 111 having an end, a grafting portion 112 having an end, and a distal region (not shown) having an end, the second bottom beam 160 configured for contacting the second bottom-lateral surface 124 of the central beam 101 and the second bottom-side surface 134 of the central beam 101 in the expanded state 149e, the central axis of the second bottom beam being at least substantially on (i) the bottom plane and (ii) a second side plane containing the central axis of the second bottom beam and the second top beam.

In some embodiments, the central axis of the first top beam 150 can be at least substantially parallel to the central beam axis 105. Likewise the frame 149 can be configured to have a second top beam 160 including a proximal portion 111 having an end, a grafting portion 112 having an end, and a distal portion (not shown) having an end, the second top beam 160 configured for contacting the second top-lateral surface 119 of the central beam 101 and the second top-side surface 132 of the central beam 101 in the expanded state 149e, the central axis of the second top beam 160 being at least substantially parallel to the central beam axis 105. Likewise the frame 149 can be configured to have a first bottom beam 170 including a proximal portion 111 having an end, a grafting portion 112, and a distal portion (not shown) having an end, the first bottom beam 170 configured for contacting the first bottom-lateral surface 122 of the central beam 101 and the first bottom-side surface 129 of the central beam 101 in the expanded state 149e, the central axis of the first bottom beam 170 being at least substantially parallel to the central beam axis 105. Likewise the frame 149 can be configured to have a second bottom beam 180 including a proximal portion 111 having an end, a grafting portion 112 having an end, and a distal region (not shown) having an end, the second bottom beam 160 configured for contacting the second bottom-lateral surface 124 of the central beam 101 and the second bottom-side surface 134 of the central beam 101 in the expanded state 149e, the central axis of the second bottom beam 180 being at least substantially parallel to the central beam axis 105.

Figure 1D:
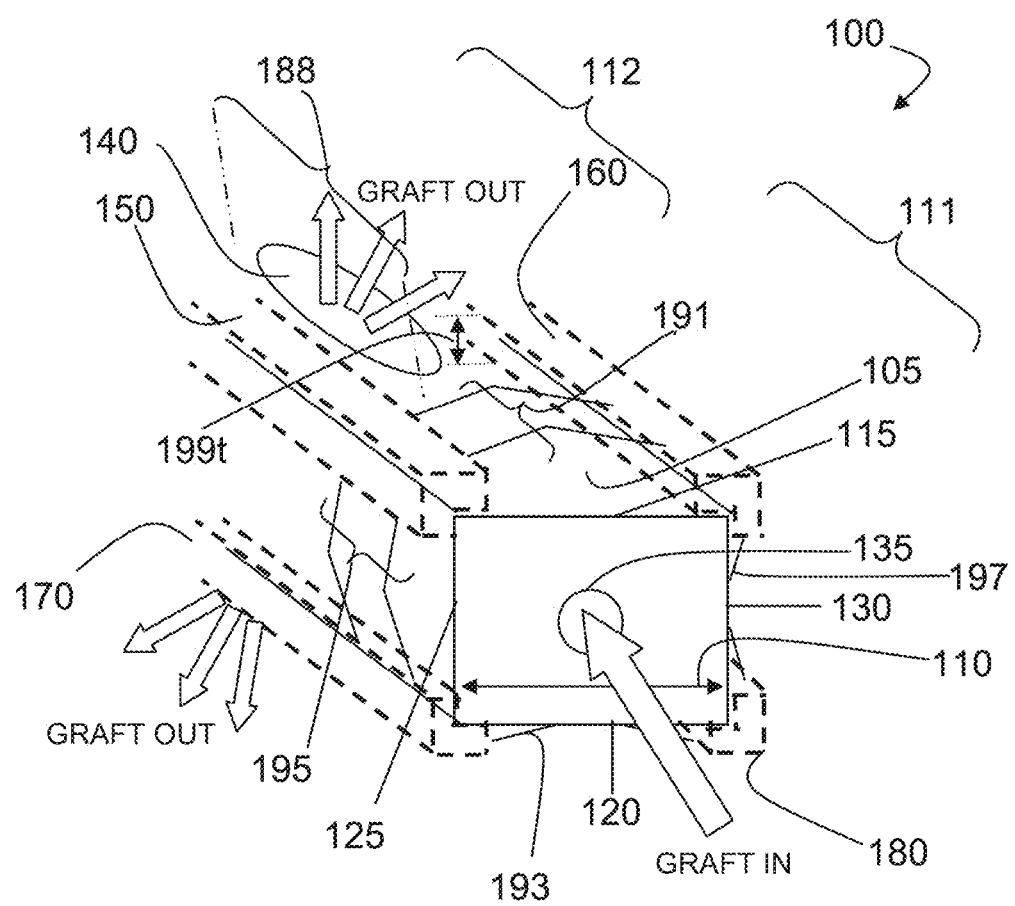

As shown in FIG. 1D, the graft distribution systems provided herein have the layered effect from the frame on the central beam that provides an additive dimension, both laterally and vertically. The added dimension allows for a low profile entry of the system into the intervertebral disc space, a wide lateral profile after expansion in vivo to avoid backout, as well as a sleeve for safe insertion of the central beam between the top endplate and bottom endplate in the intervertebral space. In some embodiments, the first top beam, second top beam, first bottom beam, and second bottom beam can each have a transverse cross-sectional wall thickness adding to the respective central beam dimension, the thickness ranging from about 0.5 mm to about 5.0 mm, from about 0.75 mm to about 4.75 mm, from about 1.0 mm to about 4.5 mm, from about 1.25 mm to about 4.25 mm, from about 1.5 mm to about 4.0 mm, from about 1.75 mm to about 3.75 mm, from about 2.0 mm to about 3.5 mm, from about 2.25 mm to about 3.25 mm, or any range therein in increments of 0.05 mm. In some embodiments, the first top beam, second top beam, first bottom beam, and second bottom beam can each have a transverse cross-sectional wall thickness adding to the respective central beam dimension, the thickness ranging from about 1.5 mm to about 2.5 mm, including 1.5, 1.75, 2.0, 2.25, 2.5, or an amount therein in increments of 0.05 mm.

The beams of the laterovertically-expanding frame 149 can be operably connected through connector elements. As such, the frame 149 can include a plurality of proximal top connector elements 191 configured to expandably connect the proximal portion 111 of the first top beam 150 to the proximal portion 111 of the second top beam 160, the expanding consisting of a flexing at least substantially on a top plane containing the central axis of the first top beam 150 and the central axis of the second top beam 160. Likewise the frame 149 can be configured to have a plurality of distal top connector elements (not shown) configured to expandably connect the distal portion of the first top beam 150 to the distal portion of the second top beam 160, the expanding consisting of a flexing at least substantially on the top plane.

Likewise the frame 149 can be configured to have a plurality of proximal bottom connector elements 193 configured to expandably connect the proximal portion 111 of the first bottom beam 170 to the proximal portion 111 of the second bottom beam 180, the expanding consisting of a flexing at least substantially on a bottom plane containing the central axis of the first bottom beam 170 and the central axis of the second bottom beam 180. Likewise the frame 149 can be configured to have a plurality of distal bottom connector elements (not shown) configured to expandably connect the distal portion of the first bottom beam 170 to the distal portion of the second bottom beam 180, the expanding consisting of a flexing at least substantially on the bottom plane.

Likewise the frame 149 can be configured to have a plurality of proximal first side connector elements 195 configured to expandably connect the proximal portion 111 of the first top beam 150 to the proximal portion 111 of the first bottom beam 170, the expanding consisting of a flexing at least substantially on a first side plane containing the central axis of the first top beam 150 and the central axis of the first bottom beam 170; a plurality of distal first side connector elements (not shown) configured to expandably connect the distal portion of the first top beam 150 to the distal portion of the first bottom beam 170, the expanding consisting of a flexing at least substantially on the first side plane. Likewise the frame 149 can be configured to have a plurality of proximal second side connector elements 197 configured to expandably connect the proximal portion 111 of the second top beam 160 to the proximal portion 111 of the second bottom beam 170, the expanding consisting of a flexing at least substantially on a second side plane containing the central axis of the second top beam 160 and the central axis of the second bottom beam 180; a plurality of distal second side connector elements (not shown) configured to expandably connect the distal portion of the second top beam 160 to the distal portion of the second bottom beam 180, the expanding consisting of a flexing at least substantially on the second side plane.

In some embodiments, each plurality of proximal connector elements can be configured as proximal struts in an at least substantially parallel alignment in the expanded state and the collapsed state; and, each plurality distal connector elements are distal struts can be configured in an at least substantially parallel alignment in the expanded state and the collapsed state. As such, the proximal top struts can be configured monolithically integral to the first top beam and the second top beam and adapted to flex toward the distal top struts during collapse; and, the distal top struts can be configured monolithically integral to the first top beam and the second top beam and adapted to flex toward the proximal top struts during collapse. Likewise, the proximal bottom struts can be configured monolithically integral to the first bottom beam and the second bottom beam and adapted to flex toward the distal bottom struts during collapse; and, the distal bottom struts can be configured monolithically integral to the first bottom beam and the second bottom beam and adapted to flex toward the proximal bottom struts during collapse. Likewise, the proximal first side struts can be configured monolithically integral to the first top beam and the first bottom beam and adapted to flex toward the distal first side struts during collapse; and, the distal first side struts can be configured monolithically integral to the first top beam and the first bottom beam and adapted to flex toward the proximal first side struts during collapse. Likewise, the proximal second side struts can be configured monolithically integral to the second top beam and the second bottom beam and adapted to flex toward the distal second side struts during collapse; and, the distal second side struts can be configured monolithically integral to the second top beam and the second bottom beam and adapted to flex toward the proximal second side struts during collapse.

As shown in FIG. 1D, the frame 149 can be configured for slidably engaging with the central beam 101 in vivo following placement of the central beam 101 in the intervertebral space through the annular opening, the slidably engaging including translating the central beam 101 into the frame 149 from the proximal end 11 of the frame 149 toward the distal end of the frame 149 in vivo; the translating including keeping the central beam axis 105 at least substantially coincident with the central frame axis 113 during the translating to create the graft distribution system 100 in vivo through the annular opening. The graft distribution system 100 can also be configured to form a top graft-slab depth 199t between the top surface 115 of the central beam 101 and the top vertebral endplate; and, a bottom graft-slab depth 199b (not shown) between the bottom surface 120 of the central beam 101 and the bottom vertebral endplate in vivo. And, in some embodiments, the transverse cross-section 110 of the graft distribution system 100 in vivo is greater than the maximum lateral dimension of the annular opening to avoid backout.

Figure 1E:
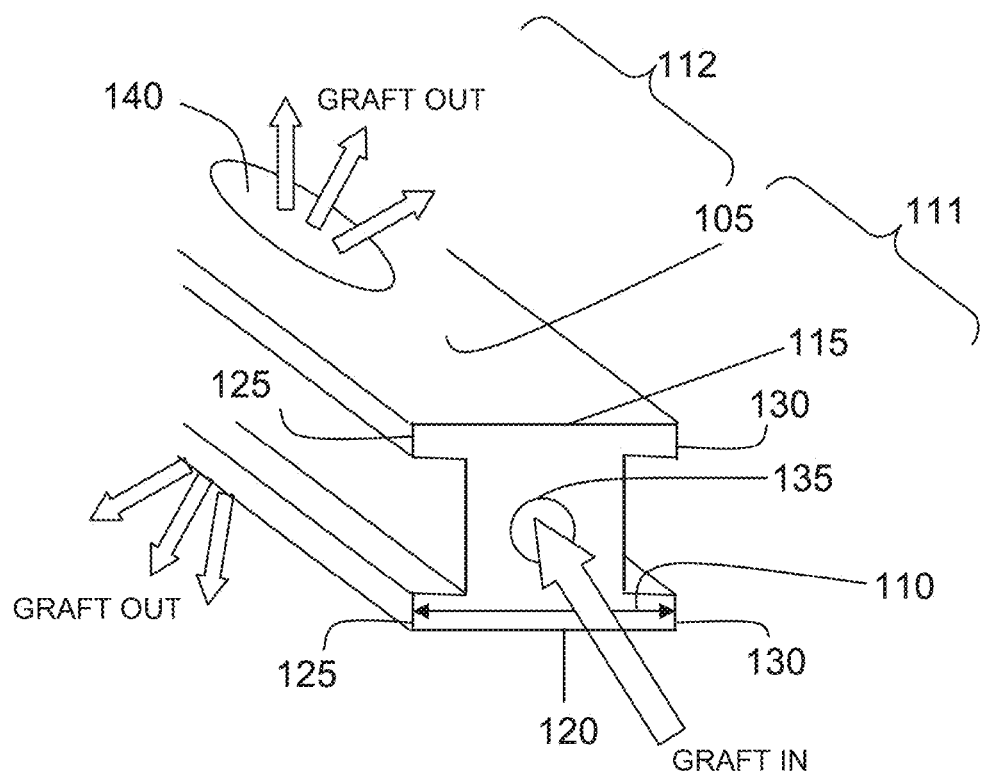
Figure 1F:
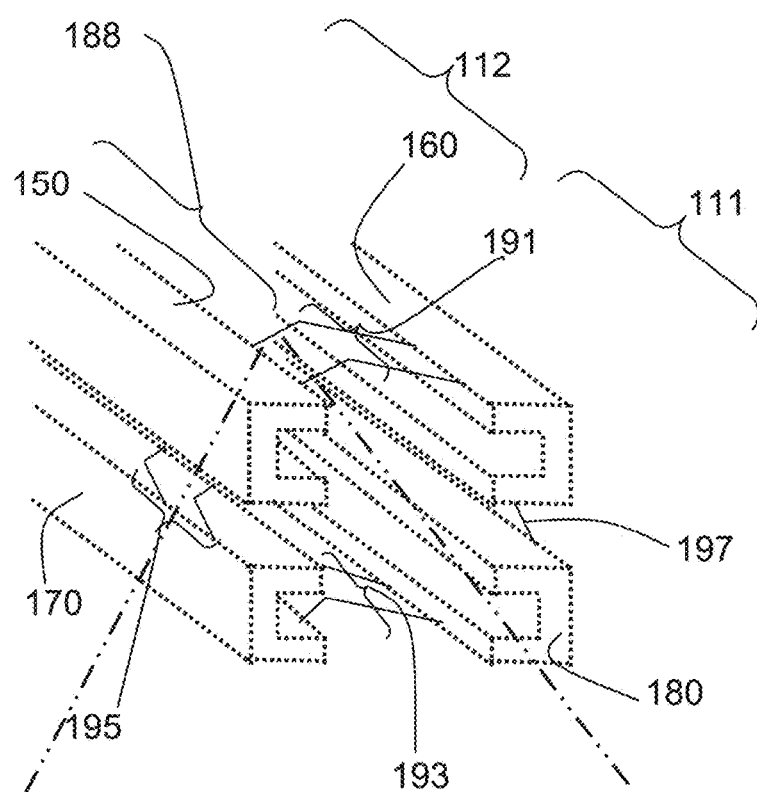

One of skill will appreciate that the central beam can have any configuration that would be operable with the teachings provided herein. In some embodiments, criteria for a suitable central beam may include a combination of a material and configuration that provides a suitable stiffness. In some embodiments, the central beam can comprise an I-beam. An example of an I-beam configuration and a complementary laterovertically expandable cage are shown in FIGS. 1E and 1F.

One of skill will further appreciate that the central beam can have any one or any combination of graft port configurations that would be operable with the teachings provided herein. In some embodiments, criteria for a suitable graft port configuration may include a combination of port size, number of ports, and placement of ports. In some embodiments, the central beam can comprise a side graft port.

Figure 1G:
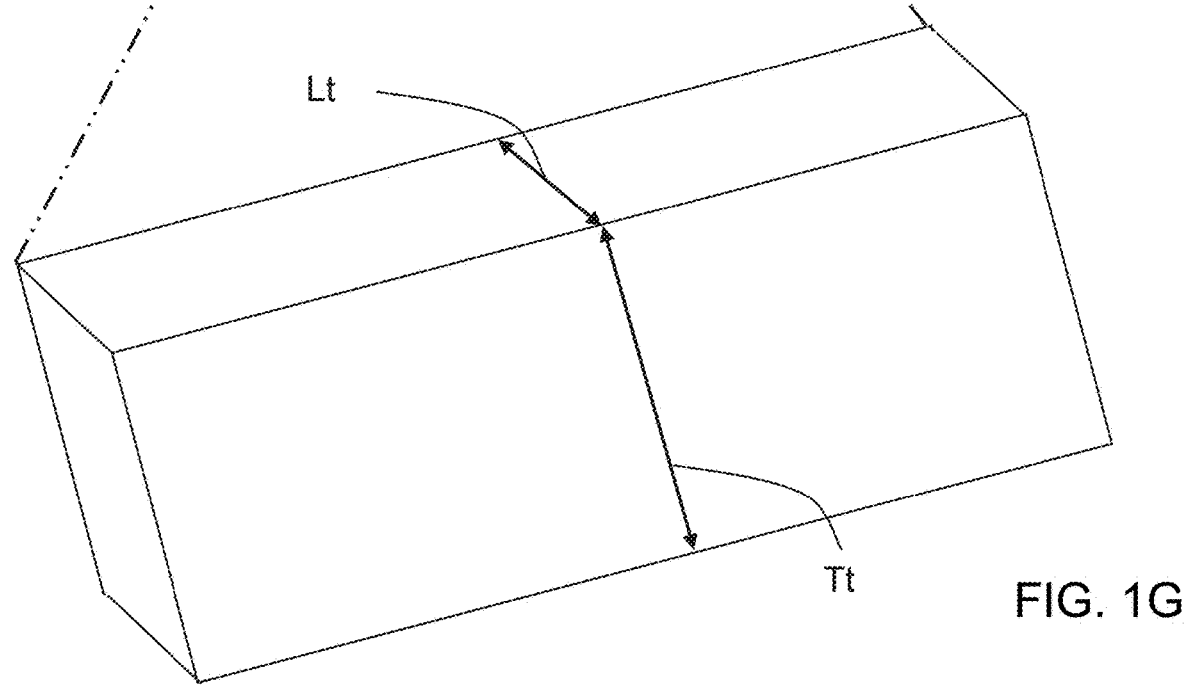
Figure 1H:
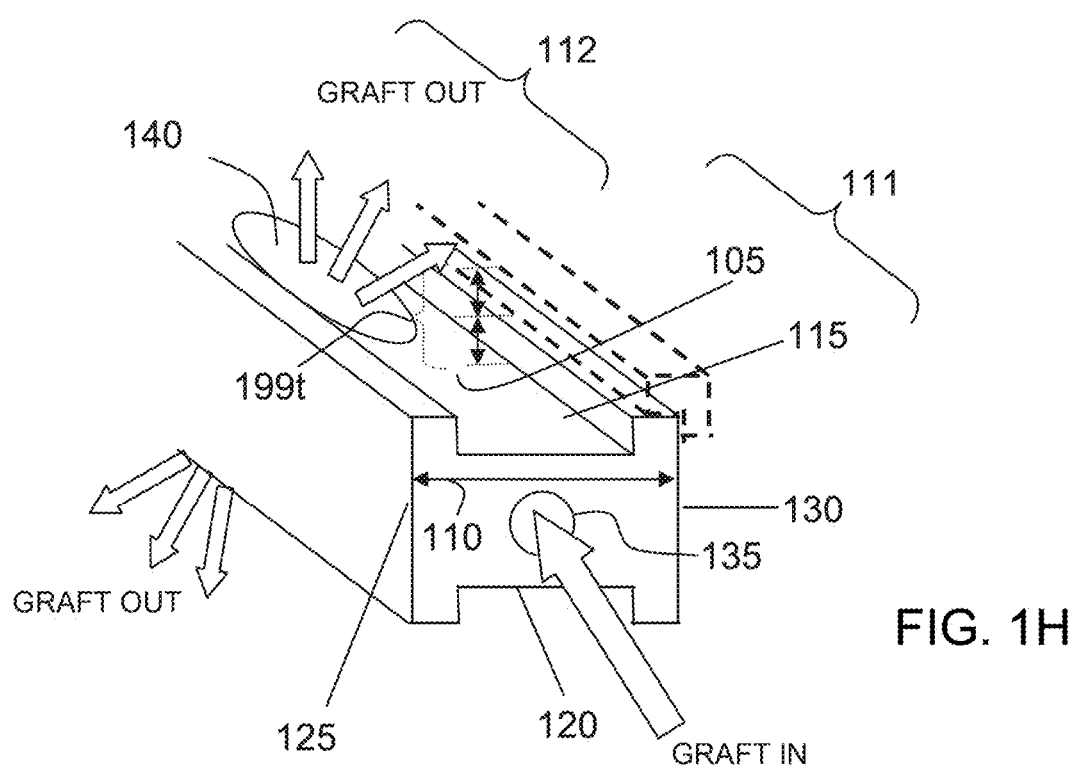
Figure 1I:
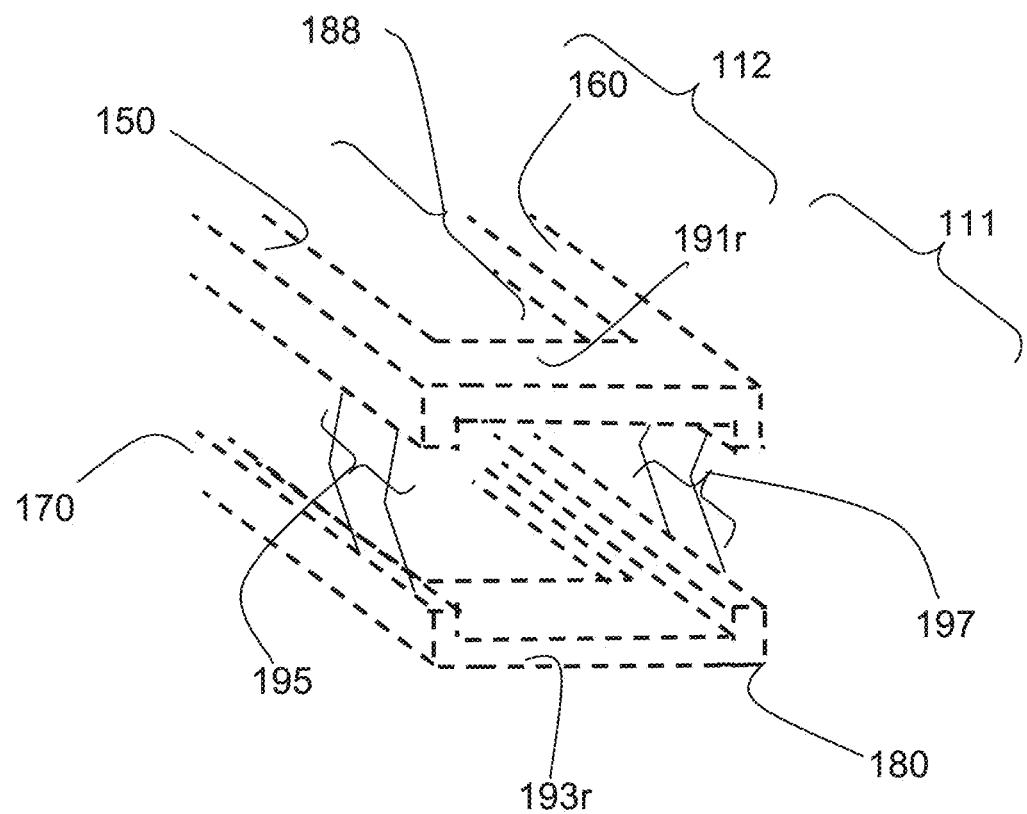

One of skill will further appreciate that the connector elements can vary in design but should meet the constraints as taught herein. In some embodiments, for example each of the connector elements 191, 193, 195, 197 can have a cross-sectional aspect ratio of longitudinal thickness to transverse thickness ranging from 1:2 to 1:8. A section of a connector element is shown in FIG. 1G.

As such, the systems can also include an improved, low-profile, intervertebral disc cage that expands bidirectionally. Consistent with the teachings herein, the cages offer several improvements to the art that include, for example, preventing the cage from backing out of the annulus fibrosis after expansion in an intervertebral disc space. As such, the terms "cage," "scaffold" and "scaffolding", for example, can be used interchangeably with "laterovertically expandable frame", "expandable frame", or "frame", in some embodiments. The cages have the ability to at least (i) laterally expand within the intervertebral space to avoid backout of the device through the annulotomy, (ii) vertically expand for distraction of the intervertebral space, (iii) provide additional space within the device in the annulus for the introduction of graft materials; (iv) maintain a large, footprint to distribute load over a larger area against the endplate, for example, by not contracting in length to expand in height and/or width; and, (v) insert into the annulus in a minimally-invasive manner using only a unilateral approach.

Figure 2A:
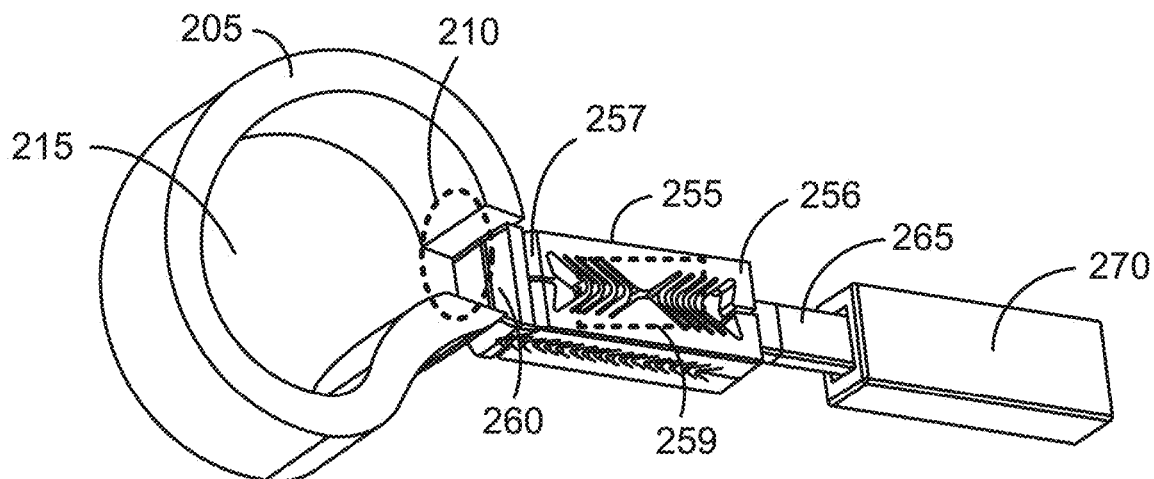
FIGS. 2A-2F illustrate a method of using a bidirectionally-expandable cage, according to some embodiments.
Figure 2B:
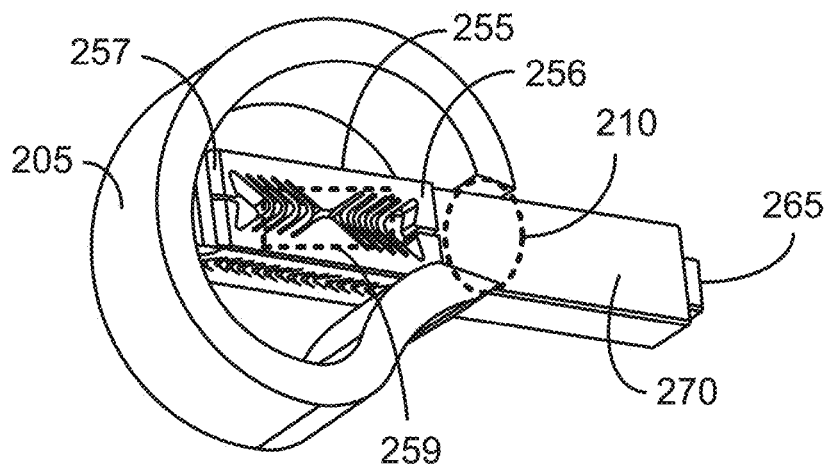

FIGS. 2A-2F illustrate a method of using a bidirectionally-expandable cage, according to some embodiments. As shown in FIGS. 2A-2B, an annulus 205 is prepared with an annulotomy serving as a single point of entry 210 and an intervertebral space 215 for insertion of a bidirectionally expandable cage system 250. As shown in FIGS. 2C-2F, the system 250 has a cage 255 having a proximal end 256, a distal end 257, and a lumen 258 that communicates with the intervertebral space 215 through an expandable/collapsible bone graft window 259; a shim core 260 having a tapered nose 262 at the distal end of the shim core 260; a releasably attachable rail beam 265; a pusher 270 that slidably translates over the shim core 260 and the rail beam 265; a trial shim 275 having a shoulder 277 and slidably translating over the rail beam 265 and shim core 260 into the lumen 258 of the cage 255, and a permanent shim 280 having a shoulder 282 and slidably translating over the rail beam 265 and shim core 260 into the lumen 258 of the cage 255.

Figure 2C:
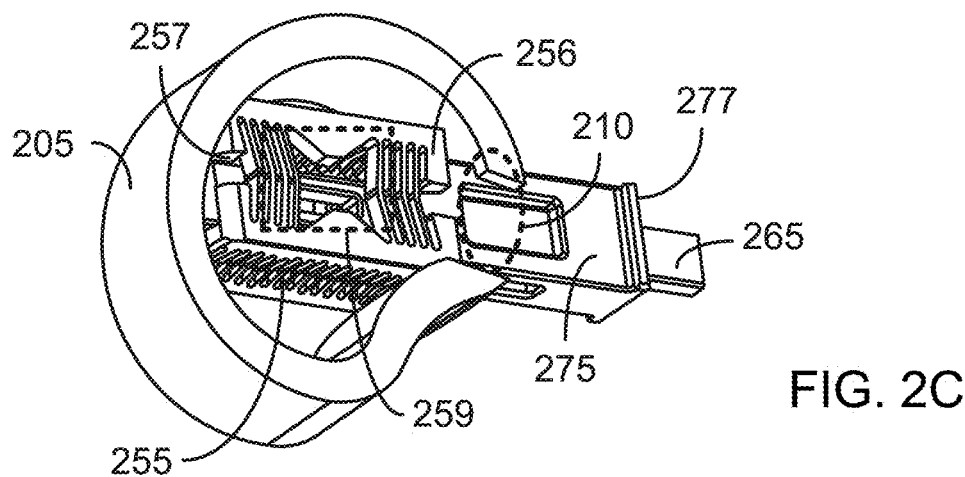
Figure 2D:
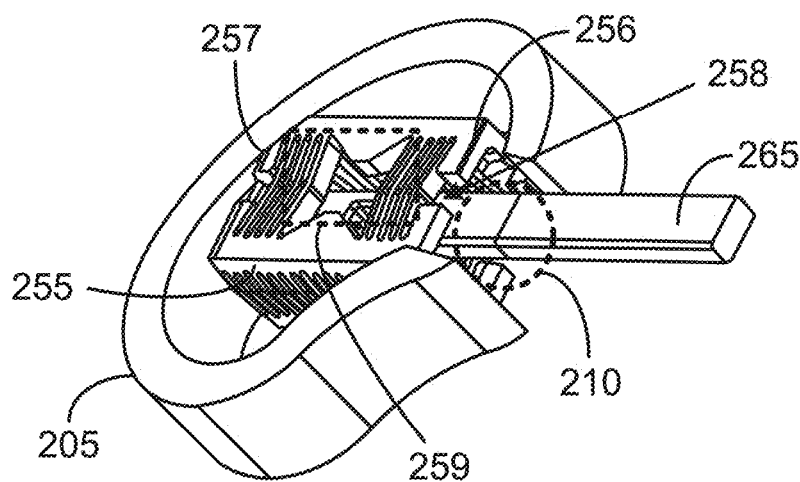
Figure 2E:
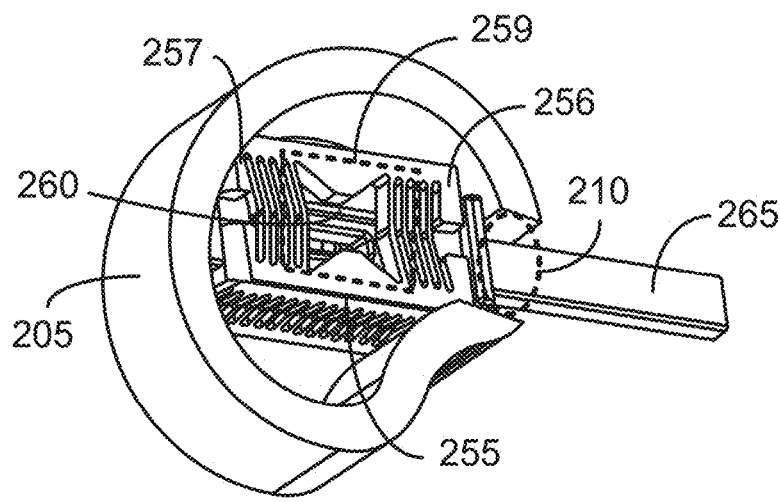
Figure 2F:
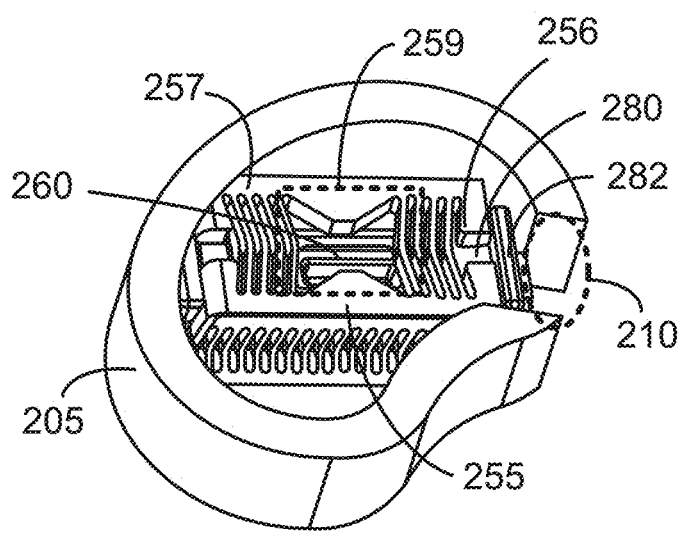

The procedure for implanting the cage 255 begins in FIG. 2A, including inserting a cannula (not shown) with a bullet-nosed obturator through the single point of entry 210 and inside the intervertebral disc space 215 until contacting the opposing wall of the annulus 205. The cannula (not shown) depth is used to select the desired length of the cage 255. The shim core 260 is loaded with bone graft material and the rail beam 265 is releasably attached to the shim core 260. The cage 255 is loaded onto the rail beam 265 and pushed onto the shim core 260 and into the cannula (not shown) using the pusher 270 until the distal end 257 of the cage 255 contacts the back of the tapered nose 262 of the shim core 260 as shown in FIG. 2A. The assembly of the shim core 260 and the cage 255 are inserted into the intervertebral space 215, and the cannula (not shown) is removed as shown in FIG. 2B. The lumen 258 of the cage 255 is loaded with bone graft material, and the trial shim 275 is slidably translated over the rail beam 265 and the shim core 260 into the lumen 258 of the cage 255 as shown in FIG. 2C. A variety of sizes of the trial shim 275 can be tested until the largest trial shim 275 that will fit is found, or until the trial shim having the desired vertical and lateral dimensions for expansion is used, in order to laterovertically expand the cage 255 as desired. The trial shim 275 is then removed, and the lumen 258 of the cage 255 is again filled with bone graft material with the shim core 260 remaining in place as shown in FIG. 2D. The permanent shim 280 is then slidably translated along the rail beam 265 and the shim core 260 into the intervertebral space 215 using the pusher 270 until the distal end 257 of the cage 255 contacts the back of the tapered nose 262 of the shim core 260 to maintain the desired laterovertical expansion of the cage 255 as shown in FIG. 2E. The rail beam 265 is then disconnected from the shim core 260 as shown in FIG. 2F.

It should be appreciated that the annulotomy can have nearly any dimension considered desirable to one of skill in the art. The annulotomy can have a vertical dimension, for example, that is the distance between a top vertebral plate and a bottom vertebral plate, the top vertebral plate and the bottom vertebral plate defining the upper and lower borders of the intervertebral disc space. In some embodiments, the vertical dimension can range from about 4 mm to about 12 mm, about 5 mm to about 11 mm, about 6 mm to about 10 mm, and about 7 mm to about 9 mm, about 6 mm to about 8 mm, about 6 mm, or any range or amount therein in increments of 1 mm. In some embodiments, the lateral dimension of the single point of entry can range from about 5 mm to about 15 mm, about 6 mm to about 14 mm, about 7 mm to about 13 mm, about 8 mm to about 12 mm, about 10 mm, or any range or amount therein in increments of 1 mm. In some embodiments, the single point of entry has an area with a diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein. The low profile dimensions of the cages taught herein are designed to fit within these dimensions.

One of skill will also appreciate that there are several methods and devices that could be used to expand the cage. In some embodiments, the expanding includes using a means for (i) laterovertically expanding the cage and (ii) creating a convex surface that at least substantially complements the concavity of a surface of a vertebral endplate that contacts the pair of top beams or the pair of bottom beams.

One of skill will also appreciate a method that distracts the intervertebral space and laterally expands the cage to avoid back-out. As such, in some embodiments, the expanding includes introducing a laterovertical expansion member into the intervertebral space through the single point of entry and into the cage, the laterovertical expansion member configured to provide a vertical force through the cage and into the top vertical endplate and bottom vertical endplate to distract the intervertebral space; and, a lateral force on the first side wall and the second side wall to expand the cage to a width that is greater than the lateral dimension of the single point of entry to prevent the bidirectionally-expandable cage from backing out of the annulus fibrosis after the expanding.

One of skill will also appreciate having a method for passing bone grafting material into the intervertebral space. As such, the laterovertical expansion member can include a port for introducing the grafting material into the intervertebral space. The methods and systems provided herein include the use of bone graft materials known to one of skill. Materials which may be placed or injected into the intervertebral space include solid or semi-solid grafting materials, bone from removed from patient's facet, an iliac crest harvest from the patient, and bone graft extenders such as hydroxyapatite, demineralized bone matrix, and bone morphogenic protein. Examples of solid or semi-solid grafting material components include solid fibrous collagen or other suitable hard hydrophilic biocompatible material. Some materials may also include swelling for further vertical expansion of the intervertebral disc space.

One of skill will also appreciate having a method for retaining the laterovertical expansion member in the cage. As such, the introducing can include engaging a ratchet mechanism comprising a protuberance on the laterovertical expansion member that engages with a strut of the cage to prevent the cage from backing out of the annulus fibrosis after the expanding. The ratchet mechanism can be, for example, similar to a zip-tie ratchet mechanism having a gear component and a pawl component. In some embodiments, the cage has the gear component, for example, including the struts; and, the laterovertical expansion member is a shim device having the pawl component, for example, a projection that can angle toward the proximal end of the expansion member or away from the direction of insertion of the shim device. In some embodiments, the cage has the pawl component, for example, including the struts; and, the laterovertical expansion member is a shim device having the gear component, for example, a series of projections. In some embodiments, a projection can angle from about 5° to about 75° toward the proximal end of the expansion member or away from the direction of insertion of the shim device.

One of skill will also appreciate having a method of designing the shape of the cage upon expansion. As such, in some embodiments, the expanding includes selecting a shim configured to create a convex surface on the top surface of the top wall to at least substantially complement the concavity of the respective top vertebral plate, and/or the bottom surface of the bottom wall to at least substantially complement the concavity of the respective bottom vertebral plate. In some embodiments, the expanding includes selecting a shim configured to vertically expand the distal end of the cage more than the proximal end of the cage. And, in some embodiments, the expanding includes selecting a shim configured to laterally expand the distal end of the cage more than the proximal end of the cage.

Figures 3A, 3B:
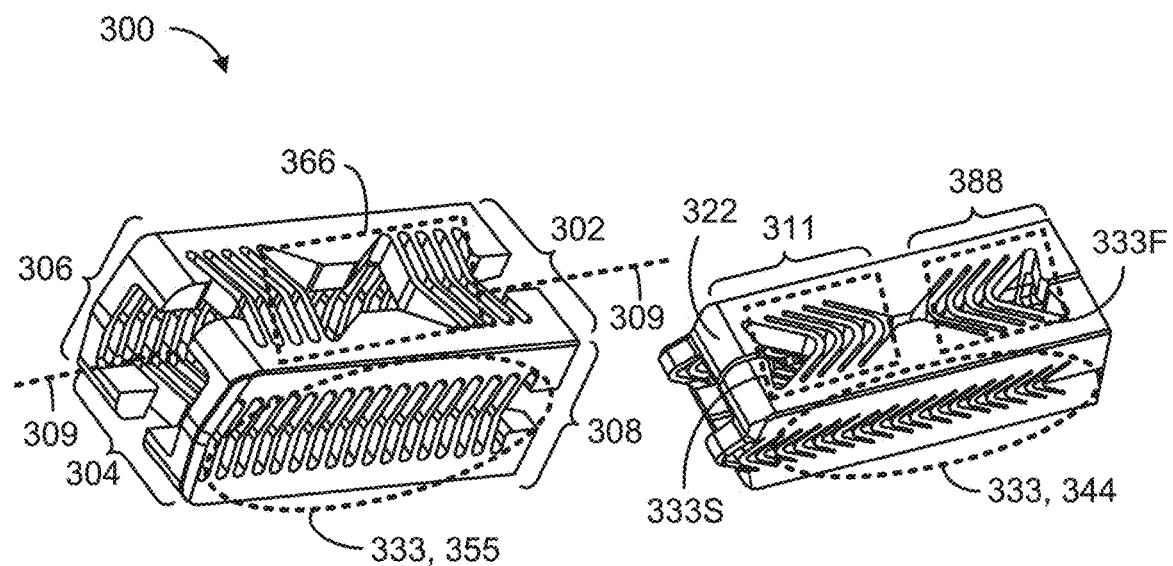
FIGS. 3A-3D illustrate a bidirectionally-expandable cage for fusing an intervertebral disc space, according to some embodiments.
Figures 3C, 3D:
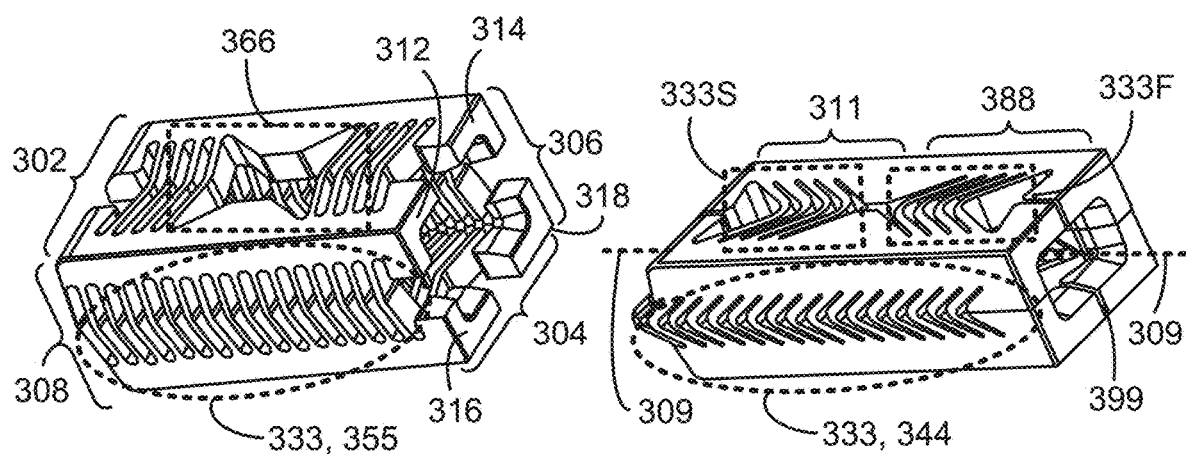

FIGS. 3A-3D illustrate collapsed and expanded views of a bidirectionally-expandable cage for fusing an intervertebral disc space, according to some embodiments. FIGS. 3A and 3C show an expanded configuration, and FIGS. 3B and 3D show a collapsed configuration. The cage 300 can comprise at least 4 walls 302,304,306,308 that form a cylinder having a long axis 309, the at least 4 walls 302, 304,306,308 including a top wall 302 forming a top plane and having a top surface with protuberances (not shown) adapted to contact the top vertebral plate (not shown); a bottom wall 304 forming a bottom plane and having a bottom surface with protuberances (not shown) adapted to contact the bottom vertebral plate (not shown); a first side wall 306 forming a first side wall plane; and, a second side wall 308 forming a second side wall plane. In these embodiments, each of the walls 302,304,306,308 can have at least 2 longitudinal beams, such that a rectangular cylinder can have a total of 4 longitudinal beams 312,314,316,318; and, a plurality of struts 333 that (i) stack in the collapsed state of the cage 300, as shown in FIGS. 3B and 3D, to minimize void space in their respective wall for a low profile entry of the cage 300 both vertically and laterally into a single point of entry (not shown) into an intervertebral disc space (not shown) and (ii) deflect upon expansion to separate the at least 2 longitudinal beams of the total of 4 longitudinal beams 312,314,316,318 in the rectangular cylinder in their respective wall 302,304,306,308. In addition, the cage 300 can be configured to expand laterally in the intervertebral space (not shown) to a size greater than a lateral dimension of the single point of entry (not shown to prevent the bidirectionally-expandable cage 300 from backing out of the annulus fibrosis (not shown) after the expanding shown in FIGS. 3A and 3C.

It should be appreciated that the collapsed configuration includes the design of a low profile entry through the annulus fibrosis to allow for a minimally-invasive procedure. In order to facilitate the use of a minimally-invasive procedure, the low profile entry of the collapsed configuration should be a substantially small area of entry having a diameter ranging, for example, from about 5 mm to about 12 mm for the single point of entry through the annulus fibrosis. In some embodiments, the low profile has an area with a diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein.

One of skill will appreciate that a variety of strut configurations may be contemplated to minimize void space for the low profile entry of the cage into the intervertebral space. In some embodiments, each wall of the cage has a series of v-shaped struts 333 that (i) stack in a closed-complementary configuration 344 in the collapsed state to minimize void space in their respective wall for the low profile entry of the cage both vertically and laterally into the intervertebral space, and (ii) deflect upon expansion in a plane that is at least substantially parallel to the plane of their respective wall to an open-complementary configuration 355 to separate the at least 2 longitudinal beams of the total of 4 longitudinal beams 312,314,316,318 in the rectangular cylinder in their respective wall and open a bone graft window 366 to pass a bone graft material into the intervertebral space in the expanded configuration. In some embodiments, the cage 300 is configured to accommodate the lateral dimension of the single point of entry ranging from about 5 mm to about 15 mm.

The v-shaped struts can be "V" shaped slots projected through each of the cage walls starting at a distance of 2 mm (0.5-4) from each corner of the cage to effectively render the "V" shaped struts in the mid region of the wall faces, in which the struts can be fabricated as continuous with L shaped beams on the corners. The slots can be cut such that they are projected perpendicular to the faces or angled distally from the outside of the cage to the inside of the cage. The distally angled projection can facilitate insertion of the shims taught herein. And, the proximal faces of the corners of the beams can also have inward, distally angled chamfers to facilitate insertion of the shims taught herein. The struts can be uniform in thickness in the proximal-distal direction. In some embodiments, the struts range from about 0.2 mm to about 1.0 mm, from about 0.3 mm to about 0.9 mm, from about 0.4 mm to about 0.8 mm, from about 0.5 mm to about 0.7 mm in thickness, or any range therein in increments of about 0.1 mm. The vertex of the "V" strut can trace along the center axis of the each of the side faces and can be radiused to dimension of 0.031" (0.005-0.062"), in some embodiments, to prevent stress cracking. Moreover, the shape of the strut or the slot projections can also be C, U, or W, in some embodiments. The struts can be 4 times thicker in the direction perpendicular to the long axis of the cage than in the direction of the long axis of the cage. In some embodiments, this thickness ratio can range from about 2× to about 8×, from about 3× to about 7×, from about 4× to about 6×, about 5×, or any range therein in increments of 1×. This thickness can help maintain a high structural stiffness and strength in the direction perpendicular to the proximal-distal axis so that the transverse cross section (perpendicular to the proximal-distal axis) shape is maintained during and after insertion of the cage into the intervertebral disc space.

In some embodiments, the angle of each strut can range from about 140°-170° as measured at the vertex in the non-stressed state. In these embodiments, the angle facilitates flexion of the legs of each strut towards each other upon moderate inward pressure to collapse the cage for insertion into the disc space. Furthermore the angled strut lies in a plane at least substantially parallel to the plane of it's respective wall, and in some embodiments to the long axis of the cage, so that the flexion does not alter the side wall thickness. This helps to maintain the low profile for insertion while maximizing the lumen size. This geometry combined with the solid beams on the corners helps ensure that the implant has a minimal change in length, less than 15% reduction in length as measured along the long axis, when expanded more than 20% vertically and/or horizontally. As such, the top and bottom of the cage that support the vertebra remain at least substantially constant in length regardless of expansion.

In some embodiments, the cage 300 has v-shaped struts 333 and a bone graft window 366 that (i) complements the v-shaped struts 333 in the collapsed configuration and (ii) opens upon expansion to pass a bone graft material into the intervertebral space in the open-complementary configuration 355, which can also be referred to as an expanded configuration. And, in some embodiments, the cage 300 has a proximal region 311, a proximal end 322, a distal region 388, a distal end 399, and at least one of the at least 4 walls 302,304,306,308 having a first series of v-shaped struts 333 that are configured to stack in a closed-complementary configuration 344 in the collapsed state to minimize void space for the low profile entry of the cage 300 into the intervertebral space; and, deflect upon expansion to an open-complementary configuration 355 to separate the at least 2 longitudinal beams of the total of 4 longitudinal beams 312,314,316,318 in the rectangular cylinder in their respective wall and open a bone graft window 366 adapted to pass a bone graft material into the intervertebral space in the expanded configuration; wherein, the first series of v-shaped struts 333F is located in the proximal region of the cage, the vertices of the first series of v-shaped struts 333F pointing away from the proximal end 322 of the cage 300 and toward the distal end 399 of the cage 300. In some embodiments, the cage 300 can further comprise a second series of v-shaped struts 333S that stack in a closed-complementary configuration 344 in the collapsed state to minimize void space for the low profile entry of the cage 300 into the intervertebral space; and, deflect upon expansion to an open-complementary configuration 355 to separate the at least 2 longitudinal beams of the total of 4 longitudinal beams 312,314,316,318 in the rectangular cylinder in their respective wall and open a bone graft window 366 adapted to pass a bone graft material into the intervertebral space in the expanded configuration; wherein, the second series of v-shaped struts 333S is located in the distal region 388 of the cage 300, the vertices of the second series of v-shaped struts 333S pointing away from the distal end 399 of the cage 300 and toward the proximal end 322 of the cage 300. In such embodiments, the strut configuration can result in the expansion of the first series of v-shaped struts 333F and the second series of v-shaped struts 333S creating a bone graft window 366 that opens to the bow-tie configuration shown in FIGS. 3A and 3C.

One of skill will also appreciate that the cage design provides flexibility in the relative amounts of lateral expansion and vertical expansion, as well as the relative amounts of expansion proximally and distally across the cage in either the lateral or vertical expansions. As such, in some embodiments, the cage is configured such that the ratio of the amount of lateral expansion to the amount of vertical expansion is variable. And, in some embodiments, the cage is configured such that the ratio of the amount of proximal expansion to the amount of distal expansion is variable for lateral expansion or vertical expansion.

Figure 4A:
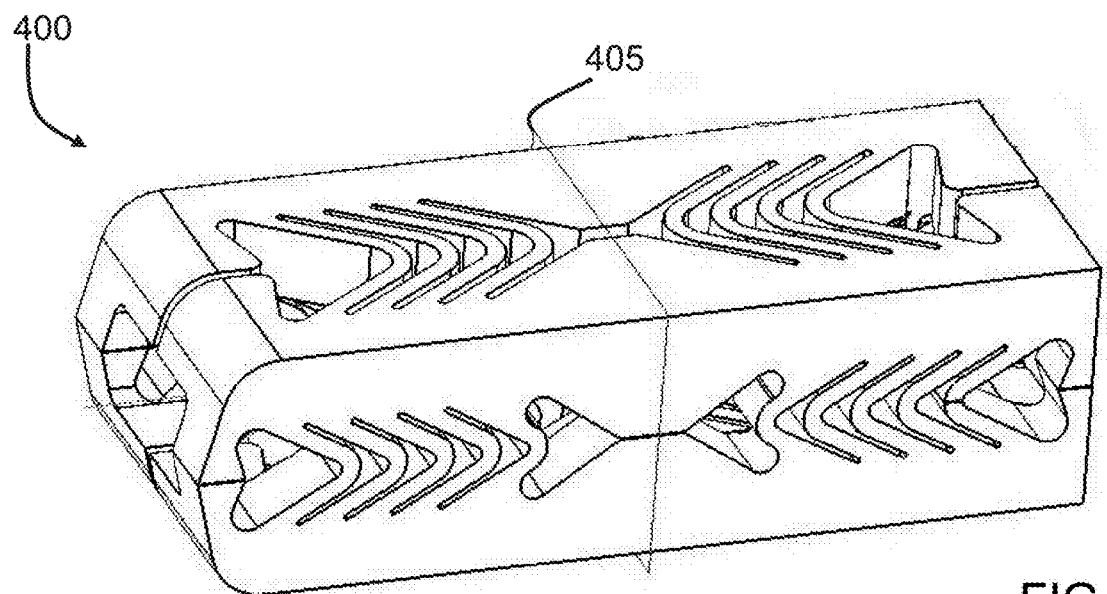
FIGS. 4A and 4B illustrate collapsed and expanded views of a bidirectionally-expandable cage having a bone graft window on each wall for fusing an intervertebral disc space, according to some embodiments.
Figure 4B:
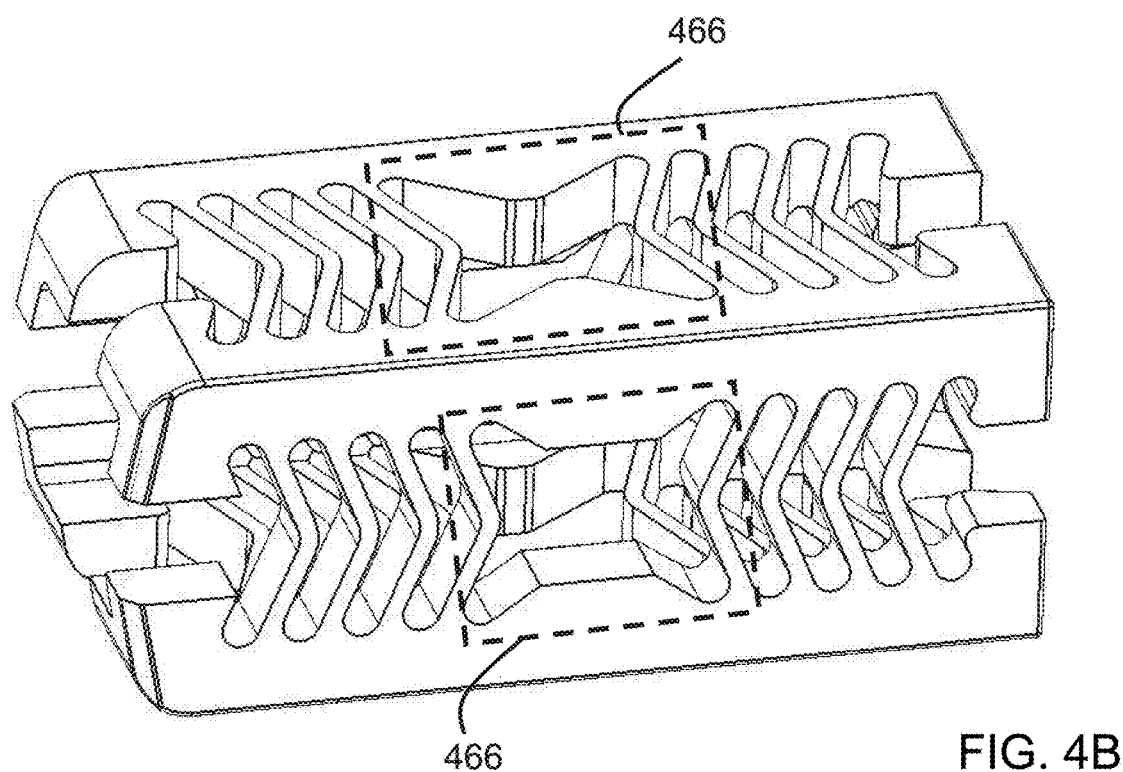
Figure 5A:
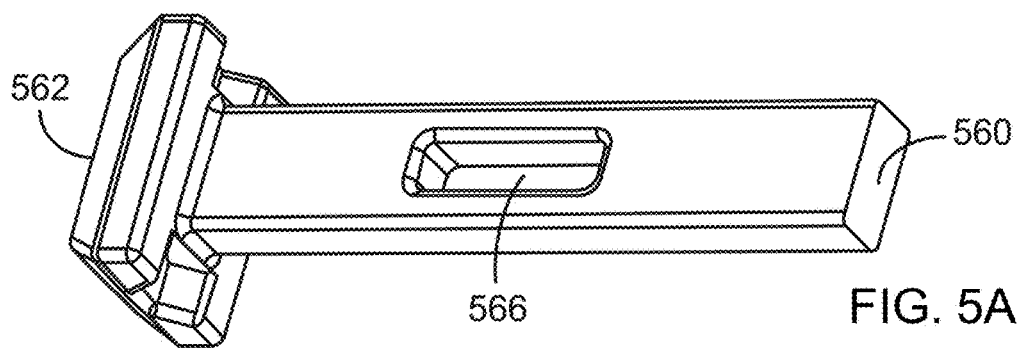
FIGS. 5A-5D illustrate system for fusing an intervertebral disc space, according to some embodiments.
Figure 5B:
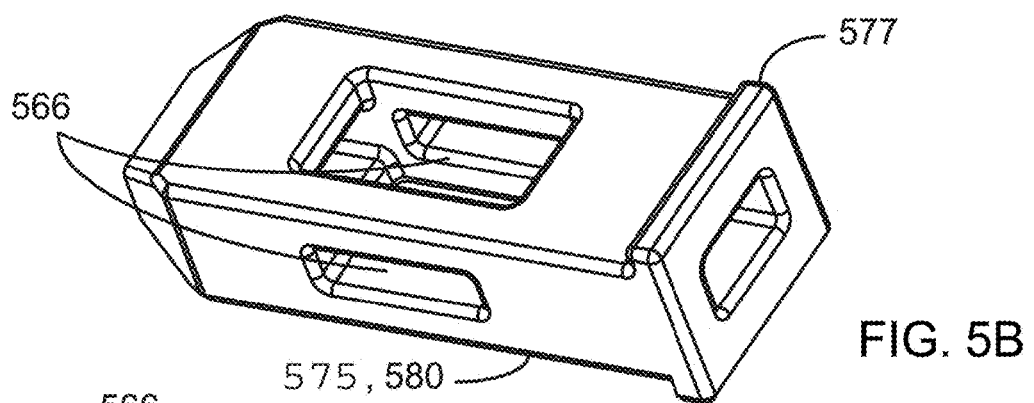
Figure 5C:
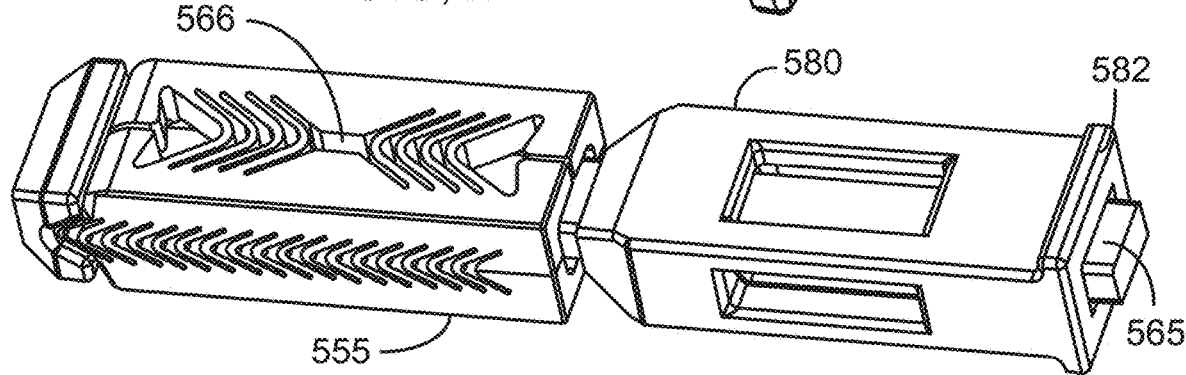
Figure 5D:
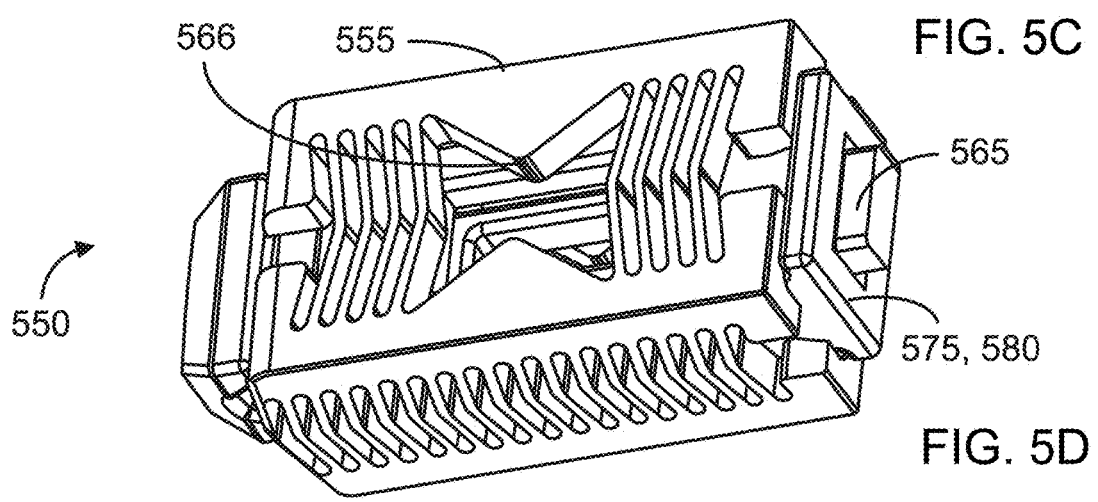

FIGS. 4A and 4B illustrate collapsed and expanded views of a bidirectionally-expandable cage having a bone graft window on each wall for fusing an intervertebral disc space, according to some embodiments. FIG. 4A shows the cage 400 in the collapsed configuration for a low-profile entry 405 into to single point of entry into an intervertebral disc space, and FIG. 4B shows the cage 400 in the expanded configuration to distract the intervertebral disc space and avoid back-out of the cage through the single point of entry after the expansion. As shown, each wall contains a bone graft window 466 for passing bone graft material into the intervertebral disc space.

FIGS. 5A-5D illustrate system for fusing an intervertebral disc space, according to some embodiments. As shown, the system 550 has a cage 555 having an expandable/collapsible bone graft window 566; a shim core 560 having a tapered nose 562 at the distal end of the shim core 560 and a bone graft window 566; a releasably attachable rail beam 565; a pusher (not shown) that slidably translates over the shim core 560 and the rail beam 565; a trial shim 575 having a shoulder 577 and slidably translating over the rail beam 565 and shim core 560 into the cage 555, and a permanent shim 580 having a shoulder 582 and slidably translating over the rail beam 565 and shim core 560 into the cage 555. The system can comprise a bidirectionally-expandable cage having at least 4 walls that form a cylinder having a long axis. The at least 4 walls can include, for example, a top wall forming a top plane and having a top surface with protuberances adapted to contact the top vertebral plate; a bottom wall forming a bottom plane and having a bottom surface with protuberances adapted to contact the bottom vertebral plate; and, a first side wall forming a first side wall plane, and a second side wall forming a second side wall plane. Each of the walls can have at least 2 longitudinal beams; and, a plurality of struts that (i) stack in the collapsed state to minimize void space in their respective wall for a low profile entry of the cage both vertically and laterally into a single point of entry into an intervertebral disc; and, (ii) deflect upon expansion to separate the at least 2 longitudinal beams in their respective wall. In some embodiments, the cage can be configured to expand laterally in the intervertebral space to a size greater than a lateral dimension of the single point of entry to prevent the bidirectionally-expandable cage from backing out of the annulus fibrosis after the expanding. Moreover, the system can include a laterovertical expansion member configured to induce the laterally expanding and the vertically expanding of the cage; and, a core configured to guide the laterovertical expansion member into the cage to induce the laterally expanding and the vertically expanding of the cage.

One of skill will appreciate that the laterovertical expansion member can also be configured to slidably engage with the core to translationally enter the cage in along the long axis of the cage. In some embodiments, the lateral expansion can occur concurrent with the vertical expansion and, in some embodiments, the lateral expansion can occur prior to the vertical expansion, for example, to reduce frictional stress on the cage during the lateral expansion. A two stage shim, for example, can be used. A first stage shim can be inserted to expand the cage laterally before inserting a second stage shim to expand the cage vertically. In some embodiments, the second stage shim can slidably translate along the first stage shim. The shim can be made of any material considered desirable to one of skill, for example, a metal or a polymer. In some embodiments, the shim can comprise a non-resorbable polymer material, an inorganic material, a metal, an alloy, or bone.

One of skill will appreciate that a system can include all or any combination of the above. As such, the teachings also include system for fusing an intervertebral disc space, the system comprising a bidirectionally-expandable cage having a proximal region, a proximal end, a distal region, a distal end, and at least 4 walls, the cage fabricated as a continuous single piece. In these embodiments, the at least 4 walls form a cylinder having a long axis and include a top wall forming a top plane and having a top surface with protuberances adapted to contact the top vertebral plate; a bottom wall forming a bottom plane and having a bottom surface with protuberances adapted to contact the bottom vertebral plate; and, a first side wall forming a first side wall plane, and a second side wall forming a second side wall plane. Each of the walls can have at least 2 longitudinal beams and a plurality of struts.

At least one of the walls can have a first series of v-shaped struts that are configured to stack in a closed-complementary configuration in the collapsed state to minimize void space for a low profile entry of the cage through a single point of entry into an intervertebral disc space; and, deflect upon expansion to an open-complementary configuration to separate the at least 2 longitudinal beams in their respective wall and open a bone graft window adapted to pass a bone graft material into the intervertebral space in the expanded configuration. The first series of v-shaped struts can be located in the proximal region of the cage, the vertices of the first series of v-shaped struts pointing away from the proximal end of the cage and toward the distal end of the cage; and, the cage can be configured to expand laterally in the intervertebral space to a size greater than a lateral dimension of the single point of entry to prevent the bidirectionally-expandable cage from backing out of the annulus fibrosis after the expanding. A laterovertical expansion member can be configured to induce the laterally expanding and the vertically expanding of the cage; and, a core can be configured to guide the laterovertical expansion member into the proximal end of the cage, and along the long axis of the cage, to expand the cage laterally and vertically. Moreover, the laterovertical expansion member can slidably engage with the core to translationally enter the cage along the long axis of the cage.

One of skill will appreciate that the systems and system components can be manufactured using any method known to one of skill in the manufacture of such intricate metal and/or polymeric components. For example, the cage can be fabricated in a partially expanded state or a fully expanded state. Moreover, the cage can be manufactured to have no internal stress or strain in the partially or fully expanded state when no external loading is applied.

The system components can comprise any suitable material, or any combination of materials, known to one of skill. For example, all components can be metal, all components can be plastic, or the components can be a combination of metal and plastic. One of skill will appreciate that the cages can have performance characteristics that are near that of a bone structure, in some embodiments, such that the scaffoldings are not too stiff or hard, resulting in a localized loading issue in which the scaffolding puts too much pressure on native bone tissue, and likewise such that the scaffoldings are too flexible or soft, resulting in a localized loading issue in which the bone tissue puts too much pressure on the scaffolding. A radio-opaque material can be employed to facilitate identifying the location and position of the scaffolding in the spinal disc space. Examples of such materials can include, but are not limited to, platinum, tungsten, iridium, gold, or bismuth.

One of skill can select materials on the basis of desired material performance characteristics. For example, one of skill will look to performance characteristics that can include static compression loading, dynamic compression loading, static torsion loading, dynamic torsion loading, static shear testing, dynamic shear testing, expulsion testing, and subsidence testing. The parameters for upper and lower limits of performance for these characteristics can fall within the range of existing such spinal devices that bear the same or similar environmental conditions during use. For example, a desired static compression loading can be approximately 5000N. A desired dynamic compression loading can have an asymptotic load level of ≥3000N at $5 \times 10^6$ cycles or ≥1500N at $10 \times 10^6$ cycles. The desired load level can range, for example, from about 1.0× to about 2.0×, from about 1.25× to about 1.75×, or any range therein in increments of 0.1×, the vertebral body compression strength. Examples of standard procedures used to test such performance characteristics include ASTM F2077 and ASTM F2624.

Examples of suitable materials can include non-reinforced polymers, carbon-reinforced polymer composites, PEEK (polyether ketone) and PEEK composites, polyetherimide (ULTEM), polyimide, polyamide or carbon fiber. Other examples include metals and alloys comprising any one or more components including, but not limited to, shape-memory alloys, nickel, titanium, titanium alloys, cobalt chrome alloys, stainless steel, ceramics and combinations thereof. In some embodiments, the components are all titanium or titanium alloy; all PEEK; or a combination of titanium or titanium alloy and PEEK. In some embodiments, the cage comprises titanium or titanium alloy, and the shim comprises PEEK. In some embodiments, the scaffolding can comprise a metal frame and cover made of PEEK or ULTEM. Examples of titanium alloys can include alloys of titanium, aluminum, and vanadium, such as $Ti_6Al_4V$ in some embodiments.

In some embodiments, the cage can be fabricated from strong and ductile polymers having a tensile modulus of about 400,000 psi or more, and a tensile strength of about 14,000 psi or more. Such polymers may also have the ability to strain more than 4% to break, and perhaps at least 20% to break in some embodiments. The materials can be stiffened by being filled with glass fibers or carbon fibers in some embodiments.

Bone ingrowth is desirable in many embodiments. As such, the scaffolding can comprise materials that contain holes or slots to allow for such bone ingrowth. Consistently, the scaffoldings can be coated with hydroxyapatite, or other bone conducting surface, for example, bone morphogenic protein, to facilitate bone ingrowth. Moreover, the surfaces of the scaffoldings can be formed as rough surfaces with protuberances, insets, or projections of any type known to one of skill, such as teeth or pyramids, for example, to grip vertebral endplates, avoid migration of the scaffolding, and encourage engagement with bone ingrowth.

The methods and systems provided herein include the use of bone graft materials known to one of skill. Materials which may be placed or injected into the intevertebral space include solid or semi-solid grafting materials, bone from removed from patient's facet, an iliac crest harvest from the patient, and bone graft extenders such as hydroxyapatite, demineralized bone matrix, and bone morphogenic protein. Examples of solid or semi-solid grafting material components include solid fibrous collagen or other suitable hard hydrophilic biocompatible material. Some materials may also include swelling for further vertical expansion of the intervertebral disc space.

The systems taught herein can be provided to the art in the form of kits. A kit can contain, for example, a cage, a vertical expansion member, and a bone graft material. In some embodiments, the kit will contain an instruction for use. The vertical expansion member can be any vertical expansion mechanism or means taught herein. For example, the vertical expansion member can be a shim. In some embodiments, the kit includes a graft-injection shim for temporarily distracting the intervertebral space, the graft-injection shim having a port for receiving and distributing the bone graft material in the intervertebral space. In these embodiments, the graft-injection shim can remain as a permanent shim or be removed and replaced with a permanent shim.

Figure 6:
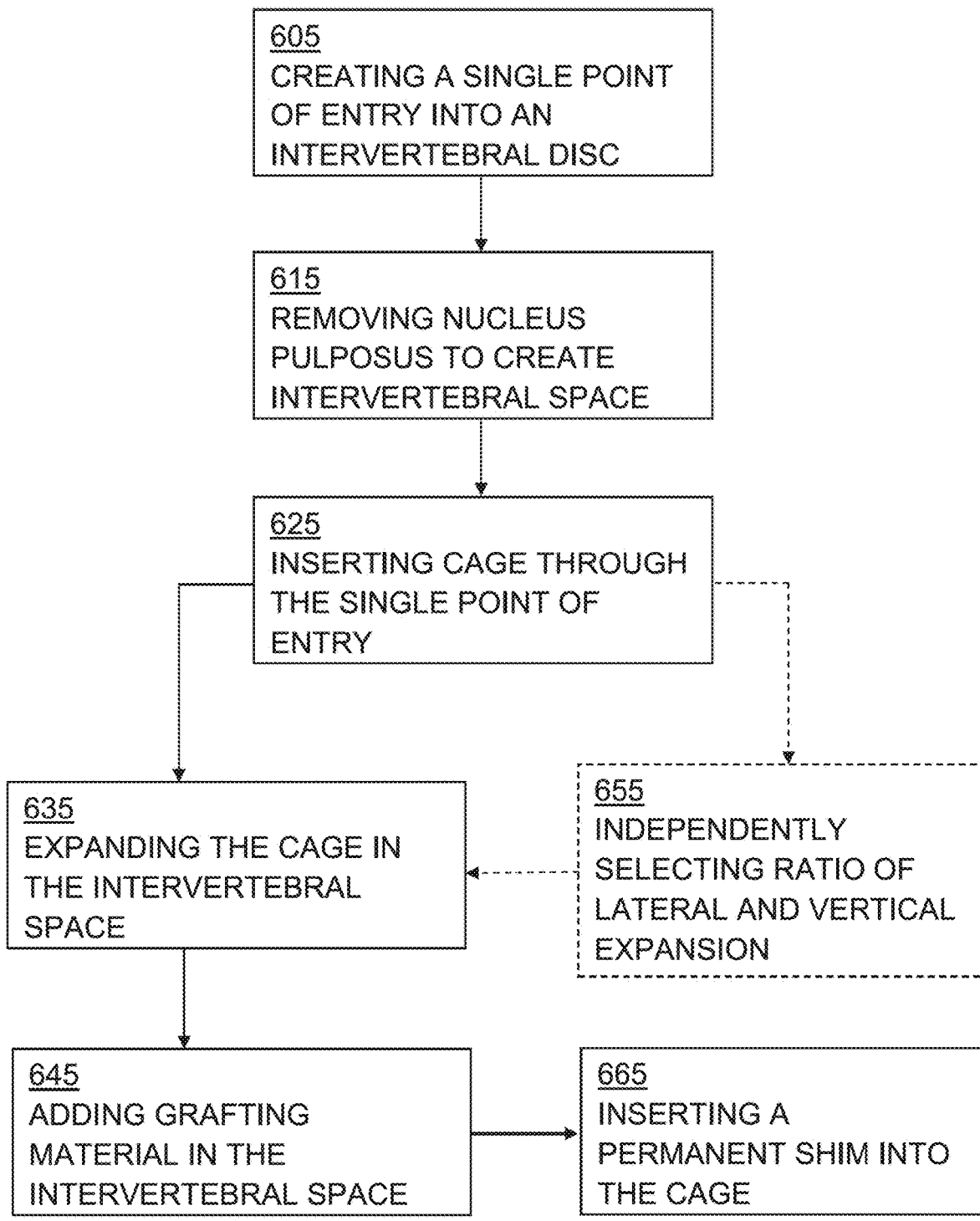
FIG. 6 is a diagram of a method of using a bidirectionally-expandable cage, according to some embodiments.
Figure 7A:
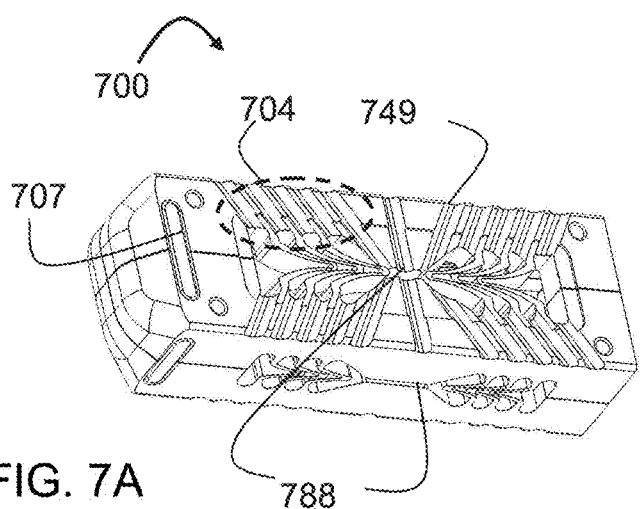
FIGS. 7A-7F illustrate some additional features of graft distribution systems, according to some embodiments.
Figure 7B:
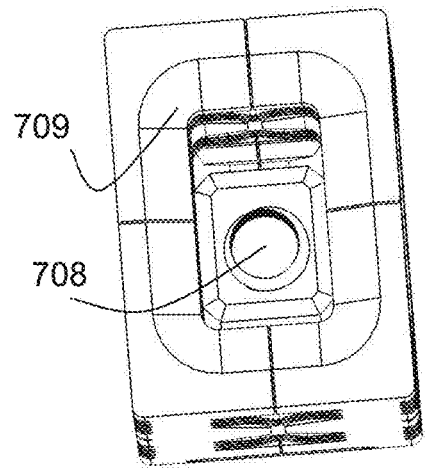
Figure 7C:
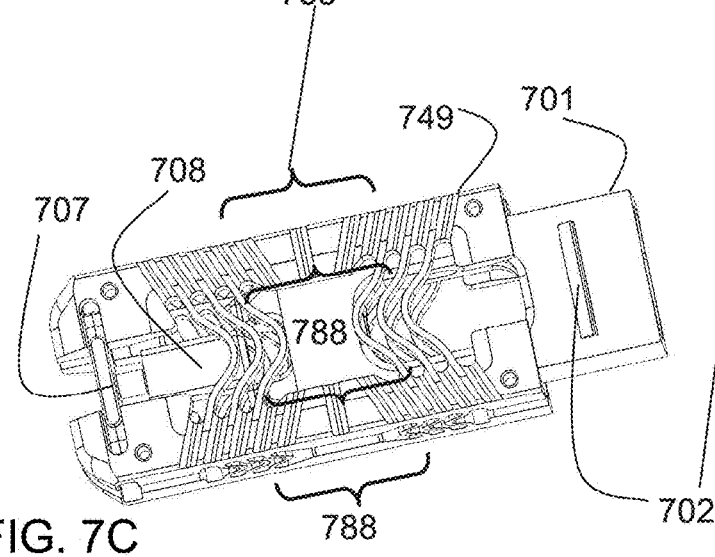
Figure 7D:
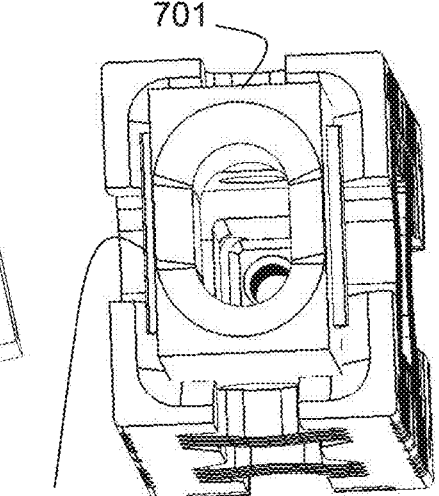
Figure 7E:
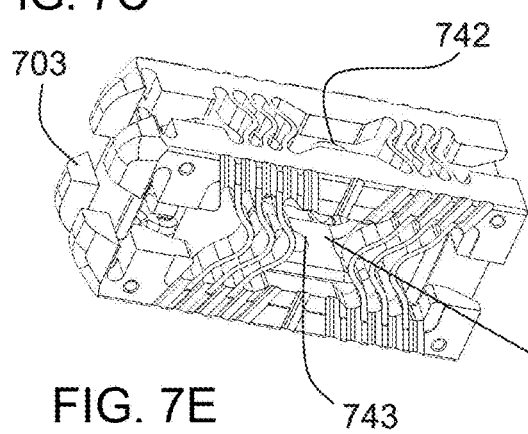
Figure 7F:
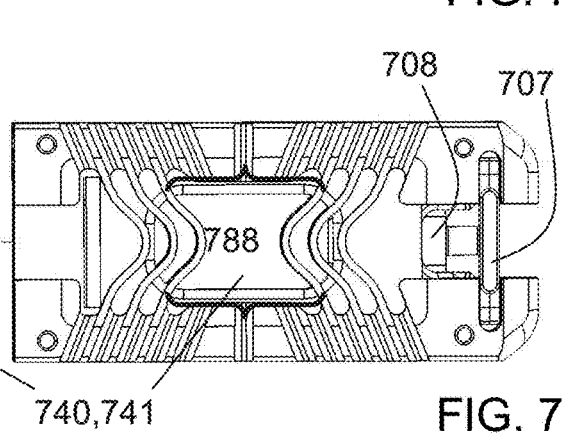

FIG. 6 is a flowchart of a method of using a bidirectionally-expandable cage, according to some embodiments. The methods can include creating 605 a single point of entry into an intervertebral disc, the intervertebral disc having a nucleus pulposus surrounded by an annulus fibrosis, and the single point of entry having a lateral dimension created through the annulus fibrosis. The methods can also include removing 615 the nucleus pulposus from within the intervertebral through the single point of entry, leaving an intervertebral space for expansion of a bidirectionally-expandable cage within the annulus fibrosis, the intervertebral space having a top vertebral plate and a bottom vertebral plate. The methods can also include inserting 625 a bidirectionally-expandable cage through the single point of entry into the intervertebral space. Moreover, the methods can include expanding 635 the cage in the intervertebral space both laterally and vertically, adding 645 a grafting material to the intervertebral space through the single point of entry, and inserting 665 a permanent shim into the cage.

One of skill will appreciate having the ability to control the amounts of vertical expansion and lateral expansion of the cage to accommodate a variety of applications, for example, to accommodate a variety annulotomy dimensions used for the single point of entry. As such, in some embodiments, the expanding 635 includes selecting 655 an amount of lateral expansion independent of an amount of vertical expansion. The lateral expanding of the cage can be selected, for example, to exceed the lateral dimension of the single point of entry through an annulotomy by a desired amount to avoid, or prevent, the cage from backing out of the intervertebral space after expansion.

As such, methods of fusing an intervertebral space are provided herein using any of the graft distribution systems taught herein. The methods can include creating a single point of entry into an intervertebral disc, the intervertebral disc having a nucleus pulposus surrounded by an annulus fibrosis, and the single point of entry having the maximum lateral dimension created through the annulus fibrosis. The methods can also include removing the nucleus pulposus from within the intervertebral disc through the single point of entry, leaving the intervertebral space for expansion of the graft distribution system within the annulus fibrosis, the intervertebral space having the top vertebral plate and the bottom vertebral plate. The methods can also include inserting the laterovertically expanding frame in the collapsed state through the single point of entry into the intervertebral space; and, inserting the central beam into the frame to form the graft distribution system. Moreover, the methods can also include adding a grafting material to the intervertebral space through the entry port.

FIGS. 7A-7F illustrate some additional features of graft distribution systems, according to some embodiments. The graft distribution systems 700 provided herein have at least a top exit port 740 and a bottom exit port 741 in the grafting portion of the central beam 701, but they can also contain side ports 742,743, such that there at least 4 graft distribution ports in some embodiments. In some embodiments, the central beam 701 further comprises a first side graft port 742 and a second side graft port 743, in addition to a locking clip 702 at the proximal end of the central beam. In some embodiments, the laterovertically-expanding frame 749 can be a monolithically integral frame, optionally having a "bullet nose" 703 at the distal end of the frame for safe position of the cage against the anterior inner annulus in vivo, and adapted to open a graft distribution window 788 on at least the top and bottom sides, as well as the first side and second side in some embodiments containing side ports, upon expansion of the connector elements to facilitate graft distribution within the intervertebral space.

The distal end of the frame 749 can be configured to have a laterovertically operable connection with a guide plate 707 that restricts the first top beam, the first bottom beam, the second top beam, and the second bottom beam to laterovertical movement relative to the guide plate when converting the frame from the collapsed state to the expanded state in vivo. And, in some embodiments, the laterovertically-expandable frame has a lumen, and the guide plate has a luminal side with a connector 708 for reversibly receiving a guide wire for inserting the laterovertically-expandable frame into the intervertebral space. In some embodiments, the frame has a chamfer inside the proximal end of the frame beams to facilitate insertion of central beam. And, in many embodiments, the frames have means for creating friction between the vertebral endplates and the frame, such as protuberances, for example cleat-type structures 704, to further avoid backout.

As can be seen in at least FIG. 7, the bone graft distribution systems provided herein include bone graft windows defined by the connector elements, the bone graft windows opening upon expansion of the laterovertically expanding frame. In some embodiments, the method further comprises opening a bone graft window, wherein the connector elements include v-shaped struts that (i) stack either proximally or distally in a closed-complementary configuration in the collapsed state to minimize void space for a low profile entry of the system both vertically and laterally into the intervertebral space, and (ii) deflect upon expansion to open the bone graft window.

It should be appreciated that the bone graft distribution systems provided herein also allow for independent expansion laterally and vertically by expanding in steps. In some embodiments, the expanding includes selecting an amount of lateral expansion independent of an amount of vertical expansion. And, in some embodiments, the lateral expansion exceeds the width of the annular opening that is the single point of entry into the intervertebral space. For example, the lateral dimension of the single point of entry can range from about 5 mm to about 15 mm in some embodiments. As such, in some embodiments, the expanding includes expanding the laterovertically expanding frame laterally to a width that exceeds the width of the single point of entry; and, inserting the central beam to expand the laterovertically expanding frame vertically to create the graft distribution system.

The bone graft distribution systems provided herein also have additional means for retaining the central beam in the laterovertically expanding frame. In some embodiments, the inserting of the central beam into the laterovertically expanding frame includes engaging a ratchet mechanism comprising a protuberance on the central beam that engages with the laterovertically-expanding frame to prevent the central beam from backing out of the laterovertically-expanding frame after the expanding.

Moreover, the bone graft distribution systems provided herein can be in the form of a kit. The kits can include, for example, a graft distribution system taught herein, a cannula for inserting the graft distribution system into the intervertebral space, a guidewire adapted for guiding the central beam into the laterovertically expanding frame, and an expansion handle for inserting the central beam into the laterovertically expanding frame to form the graft distribution system.

Figure 8A:
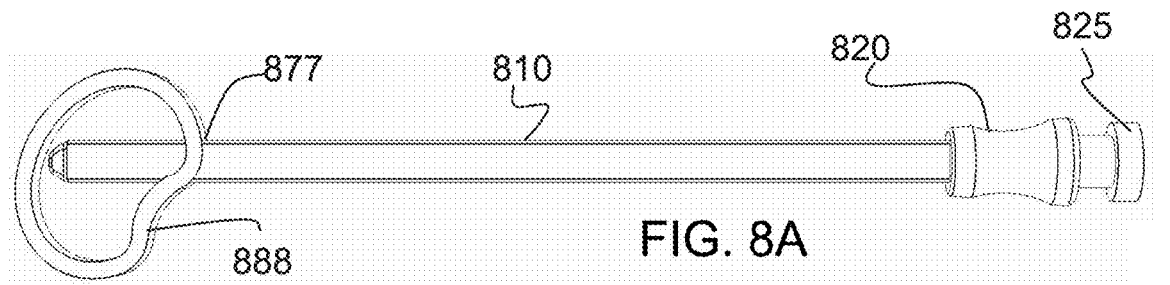
FIGS. 8A-8D illustrate components of a graft distribution kit, according to some embodiments.
Figure 8B:
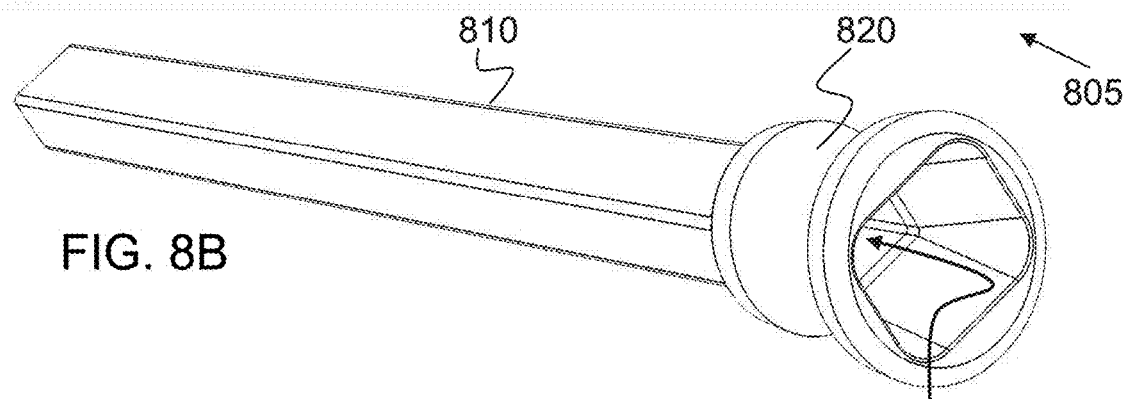
Figure 8C:
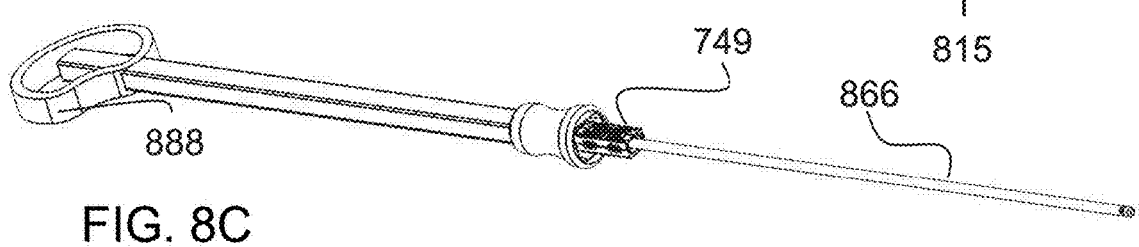
Figure 8D:
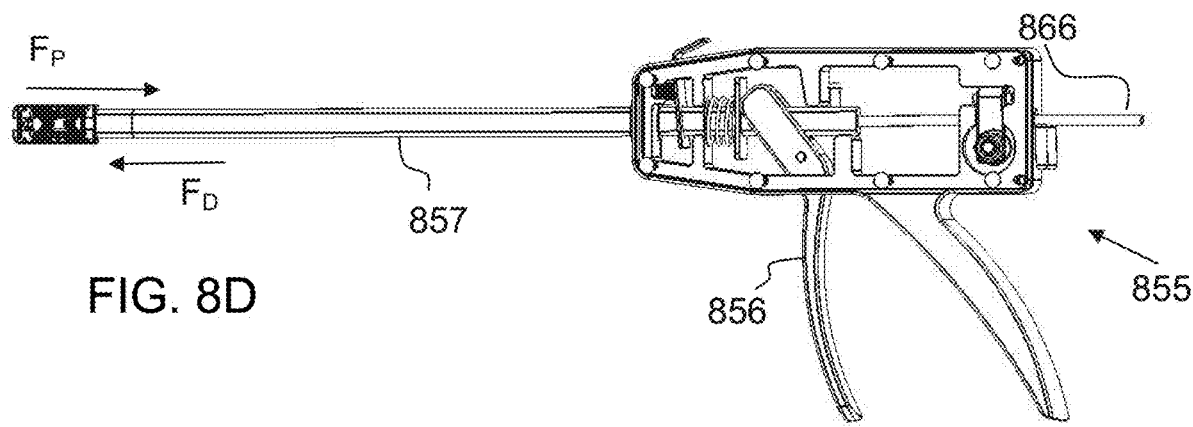

FIGS. 8A-8D illustrate components of a graft distribution kit, according to some embodiments. FIGS. 8A and 8B illustrate a 4-sided funnel cannula 805 as taught herein having a shaft 810 forming a channel 815, a funnel 820 for guiding a laterovertically expandable frame into an annulus in a low-profile configuration, the cannula shown with an obturator 825 in the channel 815 of the cannula 805, the cannula 805 inserted posterolaterally through an annulotomy 877 in the annulus 888, into an intervertebral space 899, with the distal end of the cannula 805 position near the inner anterior wall of the annulus 888. FIG. 8C illustrates FIG. 8A with a guidewire used to insert the laterovertically expandable frame 749 into the funnel 820 of the cannula 805 to guide the frame 749 into the annulus 888 in the low profile, collapsed state of the frame 749. FIG. 8D illustrates an expansion handle 855 having trigger 856 that pushes a pushrod 857 along the guidewire 866 while holding the guidewire to push on the proximal end of the central beam 701 to insert the central beam 701 into the frame 749 to expand the frame 749 by applying equal, or substantially equal forces: a proximally-directed force, $F_P$, at the connection 708 between the guide plate 707 and the guide wire 866 onto the distal portion of the beams of the frame 749, and a distally-directed force, $F_D$, at the proximal end of the central beam 701.

Figure 9A:
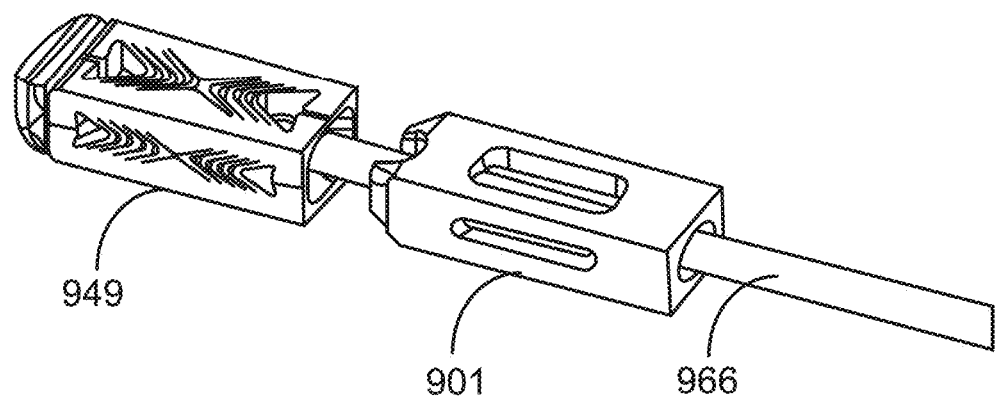
FIGS. 9A-9C illustrate the expansion of a laterovertically-expandable frame in an intervertebral space, according to some embodiments.
Figure 9B:
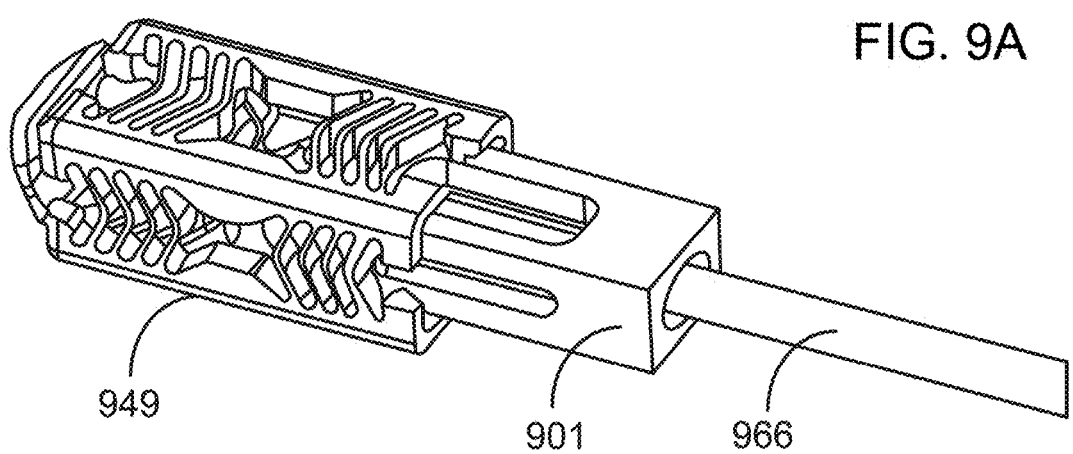
Figure 9C:
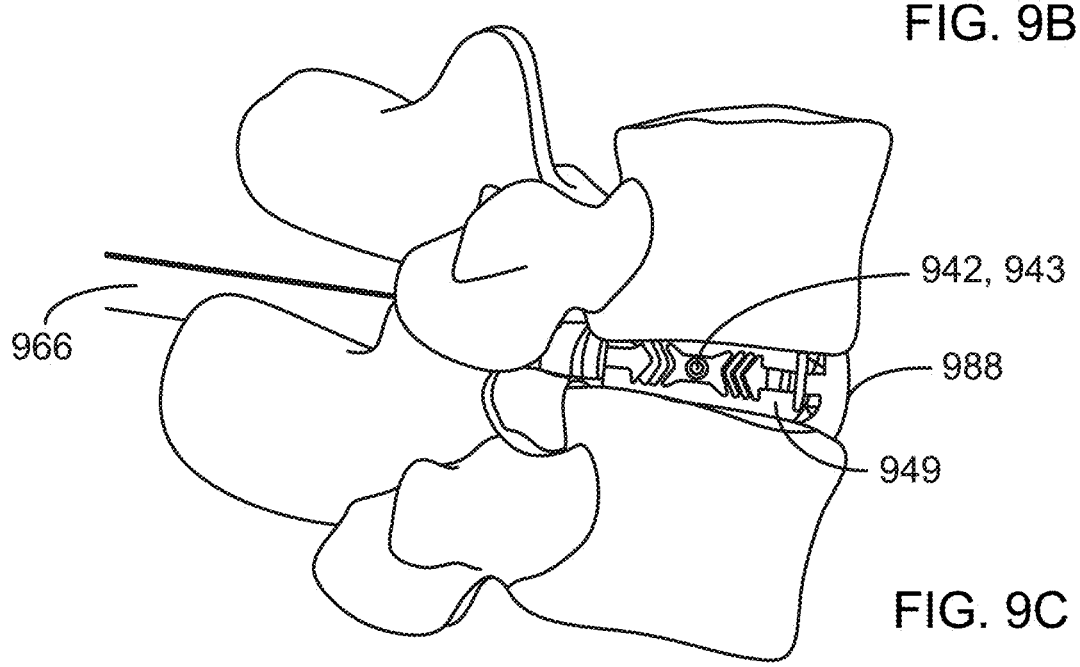

FIGS. 9A-9C illustrate the expansion of a laterovertically-expandable frame in an intervertebral space, according to some embodiments. FIG. 9A shows a collapsed frame 949 receiving a central beam 901 along a guidewire 966. FIG. 9B shows the central beam 901 partially inserted into the frame 949 in an expanded state, the guidewire 966 still in place FIG. 9C shows how the expanded state may appear when inserted posterolaterally and expanded in the intervertebral space in an annulus 988. Side ports 942,943 for bone graft distribution are shown through an open bone graft window in the expanded frame 749.

Figure 10A:
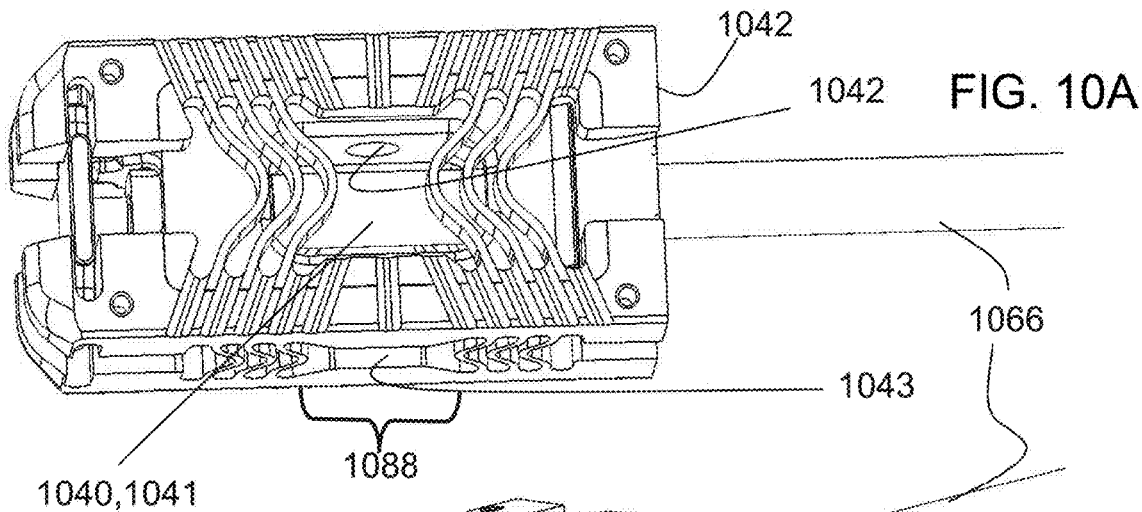
FIGS. 10A-10C illustrate profiles of an expanded graft distribution system to highlight the exit ports and bone graft windows, according to some embodiments.
Figure 10B:
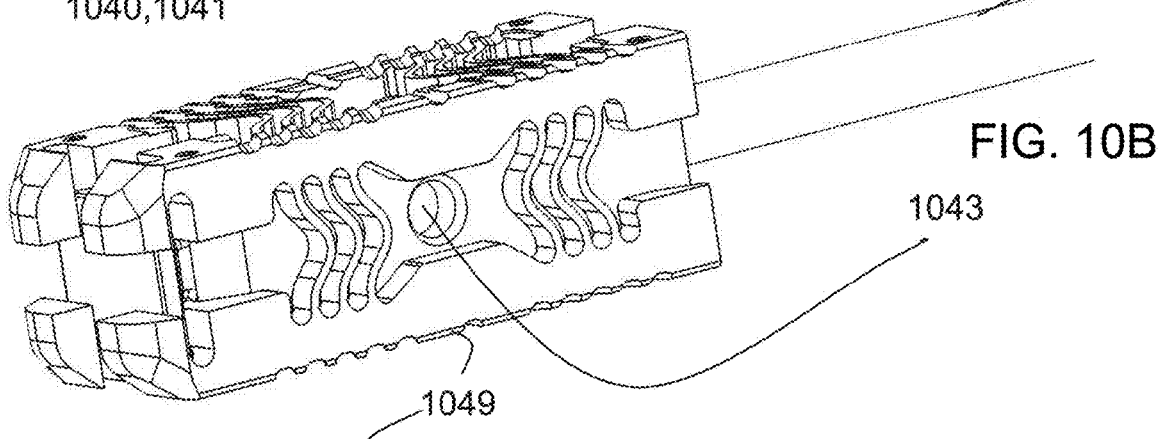
Figure 10C:
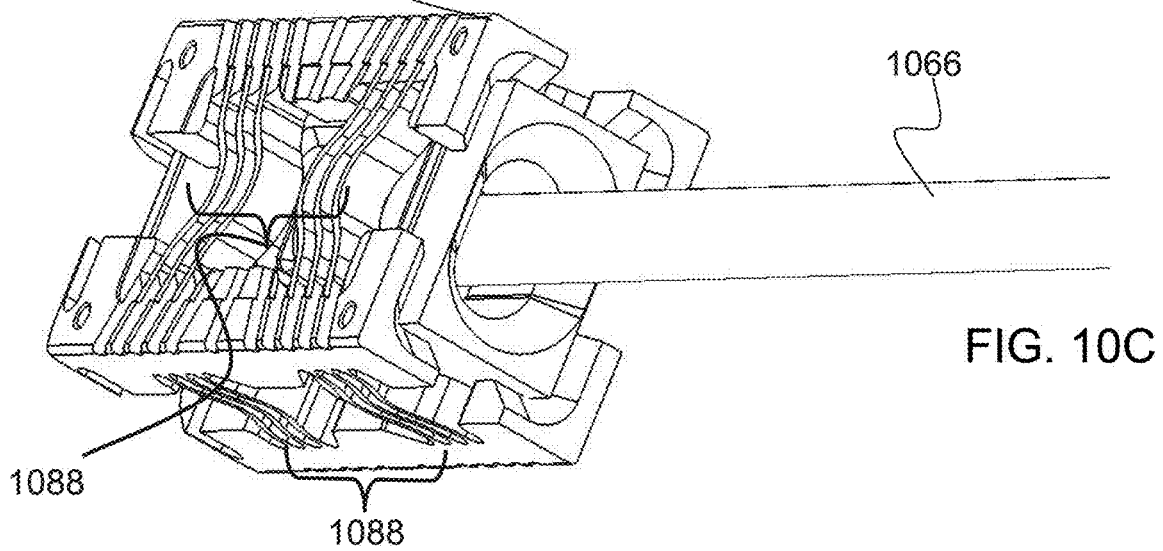

FIGS. 10A-10C illustrate profiles of an expanded graft distribution system to highlight the exit ports and bone graft windows, according to some embodiments. Profiles of an expanded frame 1049, highlighting bone graft windows 1088 and graft ports 1040, 1041, 1042, 1043 as they may appear in an intervertebral space after an implant procedure. The guidewire 1066 is shown as remaining in place.

Figure 11A:
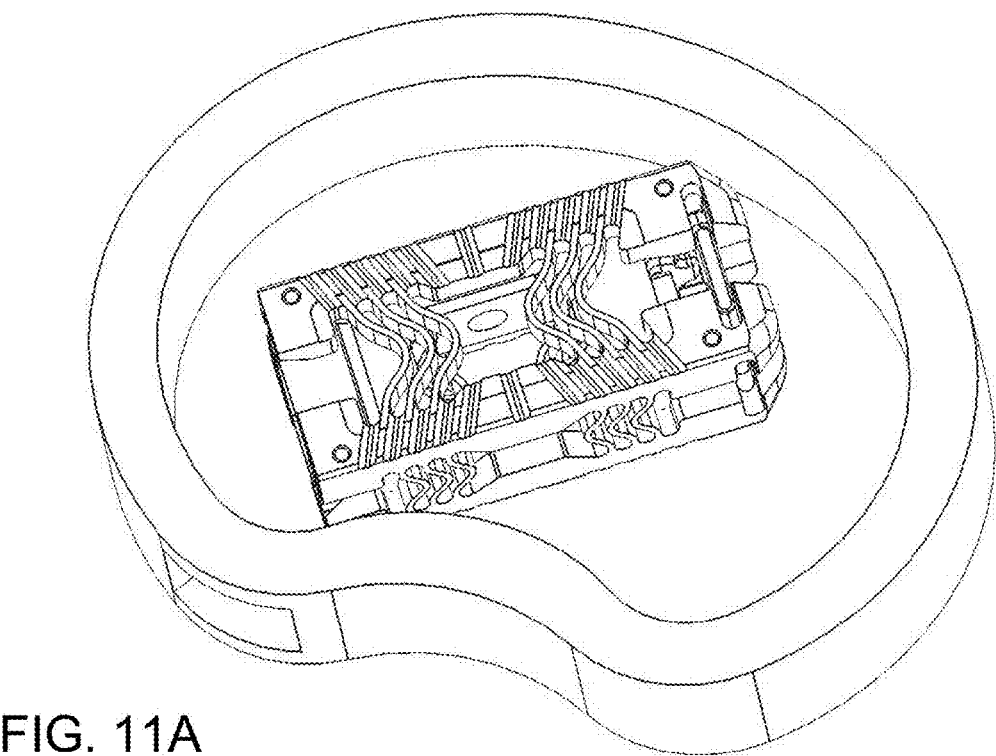
FIGS. 11A and 11B compare an illustration of the graft distribution in place to a test placement in a cadaver to show relative size, according to some embodiments.
Figure 11B:
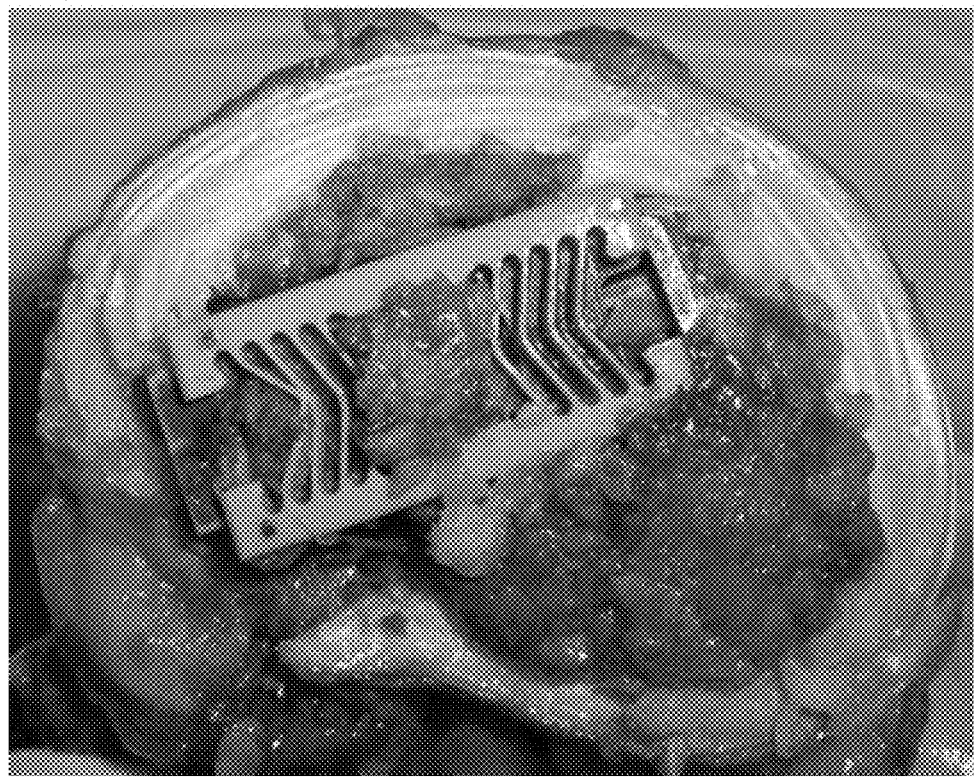
Figure 12A:
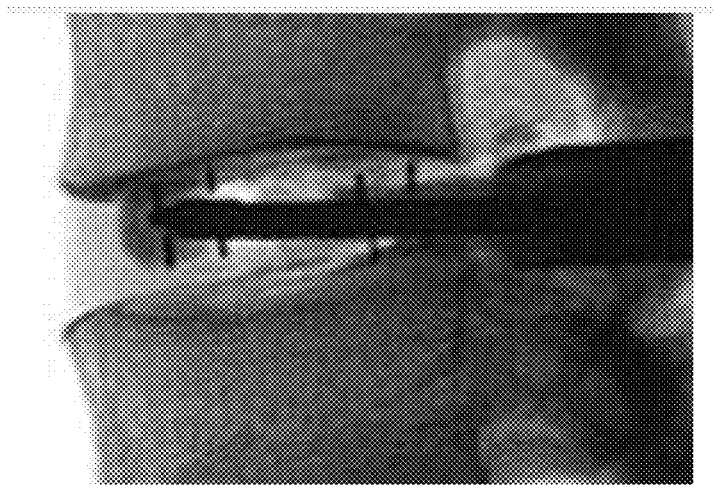
FIGS. 12A-12C show x-rays of a placement in a cadaver, according to some embodiments.
Figure 12B:
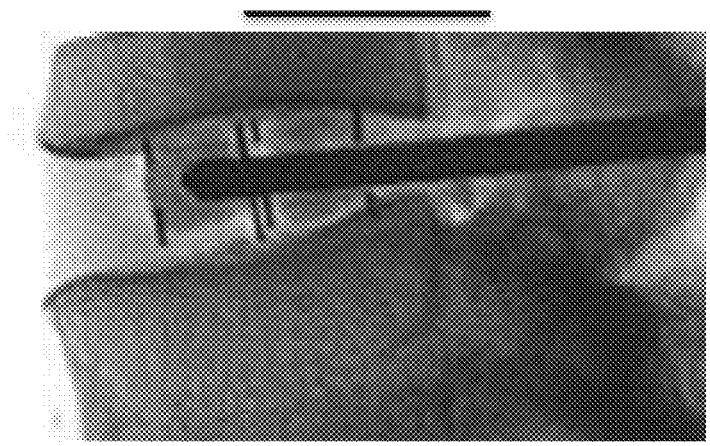
Figure 12C:
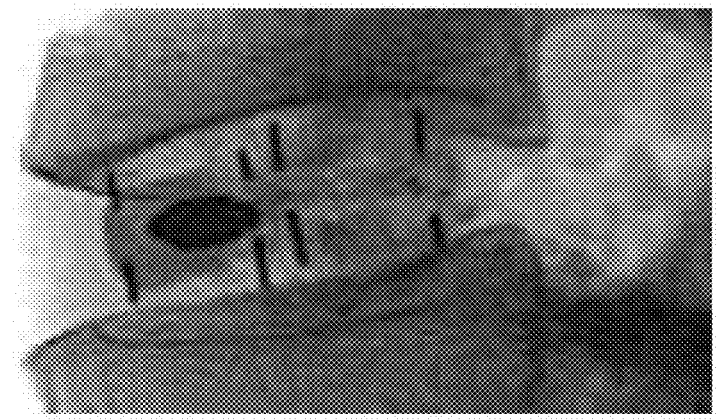

FIGS. 11A and 11B compare an illustration of the graft distribution in place to a test placement in a cadaver to show relative size, according to some embodiments. Likewise, FIGS. 12A-12C show x-rays of a placement in a cadaver, according to some embodiments.

As described above, the frame 149 can be configured such that the central axis of the first top beam 150 is at least substantially on (i) the top plane and (ii) the first side plane; the central axis of the second top beam 160 is at least substantially on (i) the top plane and (ii) the second side plane; the central axis of the first bottom beam 170 is at least substantially on (i) the bottom plane and (ii) the first side plane; and, the central axis of the second bottom beam being at least substantially on (i) the bottom plane and (ii) the second side plane. It should be appreciated that this configuration provides a "top face" framed by the first top beam and the second top beam, a "bottom face" framed by the first bottom beam and the second bottom beam, a "first side face" framed by the first top beam and the first bottom beam, and a "second side face" framed by the second top beam and the second bottom beam.

In some embodiments, it can be desirable to have the frame expand to shape that is predesigned to fit between the top endplate and the bottom endplate of the intervertebral space in a manner that calls, for example, for opposing faces of the frames to be something other than "at least substantially parallel." For example, it may be desired to have the two opposing sides of the frame expand such that the central axis of the first top beam is no longer at least substantially parallel to the central axis of the second top beam. Likewise, it may be desired to have the two opposing sides of the frame expand such that the central axis of the first bottom beam is no longer at least substantially parallel to the central axis of the second bottom beam. Likewise, it may be desired to have the opposing top and bottom sides of the frame expand such that the central axis of the first top beam is no longer at least substantially parallel to the central axis of the first bottom beam. Likewise, it may be desired to have the opposing top and bottom sides of the frame expand such that the central axis of the second top beam is no longer at least substantially parallel to the central axis of the second bottom beam. Or, any combination of the above may be desired. The laterovertically expandable frames taught herein enable each of these desirable configurations.

Figure 13A:
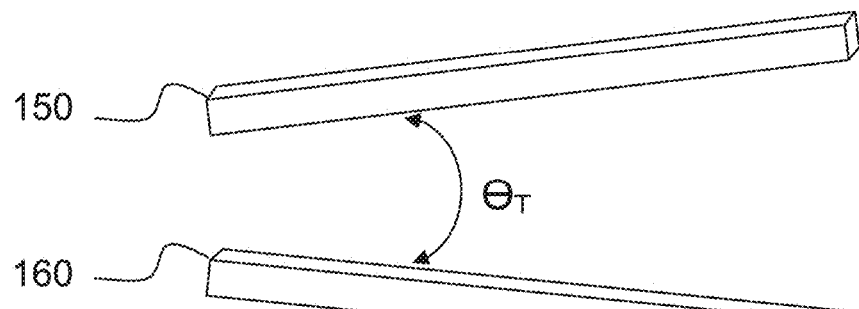
FIGS. 13A-13D show orientations of the first top beam relative to the second top beam, first bottom beam relative to the second bottom beam, first top beam relative to the first bottom beam, and the second top beam relative to the second bottom beam, according to some embodiments.
Figure 13B:
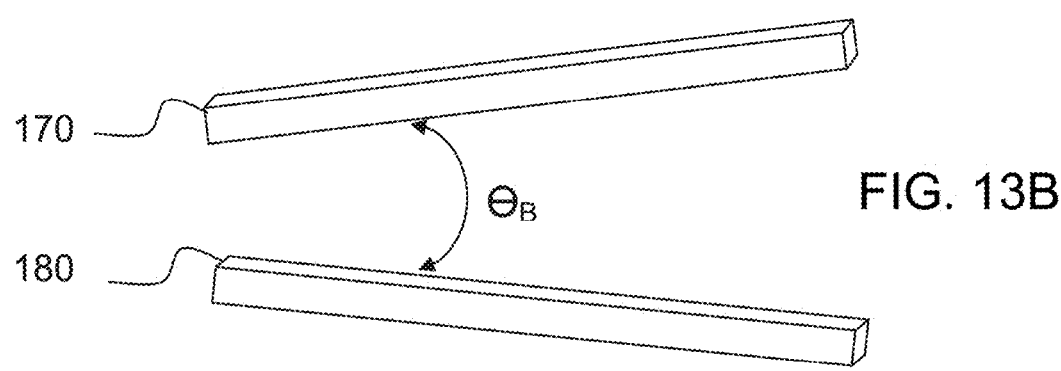
Figure 13C:
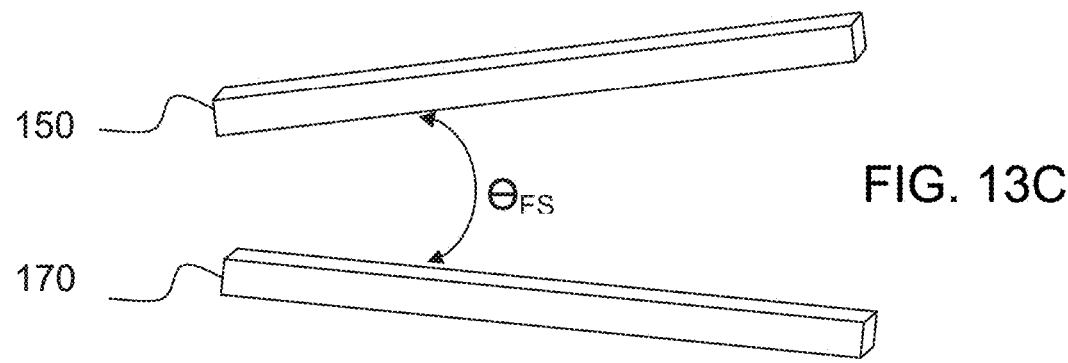
Figure 13D:
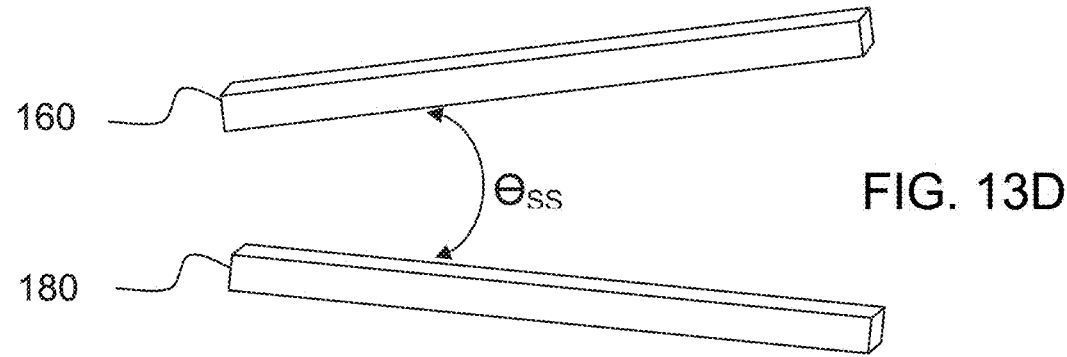

FIGS. 13A-13D show orientations of the first top beam relative to the second top beam, first bottom beam relative to the second bottom beam, first top beam relative to the first bottom beam, and the second top beam relative to the second bottom beam, according to some embodiments. FIG. 13A shows the first top beam 150 relative to the second top beam 160, in which the angle $\Theta_T$ is formed by the two beams to shape the top face of the frame. FIG. 13B shows the first bottom beam 170 relative to the second bottom beam 180, in which the angle $\Theta_B$ is formed by the two beams to shape the bottom face of the frame. FIG. 13C shows the first top beam 150 relative to the first bottom beam 170, in which the angle $\Theta_{FS}$ is formed by the two beams to shape the first side face of the frame. FIG. 13D shows the second top beam 160 relative to the second bottom beam 180, in which the angle $\Theta_{SS}$ is formed by the two beams to shape the second side face of the frame. In some embodiments, each of $\Theta_T$, $\Theta_B$, $\Theta_{FS}$, and $\Theta_{SS}$ can be independently selected and each can range from 0° to 32°, from 0.5° to 31.5°, from 0.1° to 31.0°, from 1.5° to 30.5°, from 2.0° to 30.0°, from 2.5° to 29.5°, from 3.0° to 29.0°, from 3.5° to 28.5°, from 4.0° to 28.0°, from 4.5° to 27.5°, from 5.0° to 27°, from 5.5° to 26.5°, from 6.0° to 26.0°, from 6.5° to 25.5°, from 7.0° to 25.0°, from 7.5° to 25.5°, from 8.0° to 26.0°, from 8.5° to 26.5°, from 9.0° to 26.0°, from 9.5° to 25.5°, from 10.0° to 25.0°, from 10.5° to 24.5°, from 11.0° to 24.0°, from 11.5° to 23.5°, from 12.0° to 23.0°, from 12.5° to 22.5°, from 13.0° to 22.0°, from 13.5° to 21.5°, from 14.5° to 21.0°, from 15.5° to 20.5°, from 16.0° to 20.0°, from 16.5° to 19.5°, from 17.0° to 19.0°, or any range therein in increments of 0.1°. In some embodiments, each of $\Theta_T$, $\Theta_B$, $\Theta_{FS}$, and $\Theta_{SS}$ can be independently selected and each can be about 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, or any angle therein in increments of 0.1°.

It should be appreciated that the beams can each be independently designed to have its own, independently selected curvature, whether convex or concave, and the curvatures can be the same or different between beams that share a face of the frame. And, the curvatures can be opposing for beams that form opposing faces of the frame.

Moreover, the frame can have a mixture of one or more straight and one or more curved beams.

Given the above, it should be appreciated that the frames can be designed according to nearly any opening bordered by the top vertebral endplate and bottom vertebral endplate of an intervertebral space, as well as according to a given clinical treatment regardless of the opening dimensions prior to treatment. In some embodiments, the top face of the frame can be at least substantially parallel to the bottom face of the frame, whereas the first side face of the frame and the second side face of the frame can be oriented at angles $\Theta_T$ and $\Theta_B$, wherein $\Theta_T$ and $\Theta_B$ can be independently selected to be the same or different. Likewise, in some embodiments, the first side face of the frame can be at least substantially parallel to the second side face of the frame, whereas the top face of the frame and the bottom face of the frame can be oriented at angles $\Theta_{FS}$ and $\Theta_{SS}$, wherein $\Theta_{FS}$ and $\Theta_{SS}$ can be independently selected to be the same or different. In some embodiments, each of $\Theta_T$, $\Theta_B$, $\Theta_{FS}$, and $\Theta_{SS}$ can be independently selected to range from about 5° to about 32°, from about 7° to about 22°, and from about 8° to about 16°, in some embodiments. As such, any of a variety of frames can be constructed from any of a variety of quadrilateral structures having the angles taught herein.

One of skill will appreciate that the teachings provided herein are directed to basic concepts that can extend beyond any particular embodiment, embodiments, figure, or figures. It should be appreciated that any examples are for purposes of illustration and are not to be construed as otherwise limiting to the teachings. For example, it should be appreciated that the devices provided herein can also be used as implants in other areas of the body. The devices provided herein can be used, for example, in intravertebral body procedures to support or distract intervertebral bodies in the repair of, for example, collapsed, damaged or unstable vertebral bodies suffering from disease or injury.

We claim:

1. An intervertebral scaffolding system for use in a subject, comprising:
    a central beam; and,
    an expanding frame having a collapsed state and an expanded state, the frame configured for operably contacting the central beam to create an intervertebral scaffolding system in vivo, the frame having
        a first top beam, a first bottom beam, a second top beam, and a second bottom beam; wherein, the beams are in an at least substantially parallel arrangement with each other in the expanded state;
        a plurality of connector elements configured to connect the first top beam to the second top beam, the first bottom beam to the second bottom beam, the first top beam to the first bottom beam, and the second top beam to the second bottom beam, the connecting forming a square, cylindrical shape for engaging with the central beam in vivo to support the expanding frame in the expanded state; and,
        a guide that restricts the movement of the first top beam relative to the first bottom beam, the second top beam relative to the second bottom beam, the first top beam relative to the second beam, and the first bottom beam relative to the second bottom beam during the expanding;
        wherein, the connector elements and guide maintain structural stiffness in the expanding frame in vivo to adequately support localized loading in the intervertebral space in which bone tissue puts pressure on the expanding frame.

2. The scaffolding system of claim 1, wherein the localized loading ranges from about 1.0× to about 2.0× the vertebral body compression strength of the subject.

3. The scaffolding system of claim 1, the central beam comprising an I-beam.

4. The scaffolding system of claim 1, the central beam further comprising a grafting port.

5. The scaffolding system of claim 1, wherein each of the plurality of connector elements are struts configured in an at least substantially parallel alignment in the collapsed state.

6. The scaffolding system of claim 1, wherein each plurality connector elements are struts; wherein, the struts are configured monolithically integral to the top beam and the bottom beam.

7. A method of fusing an intervertebral space using the scaffolding system of claim 1, the method comprising:
    creating a point of entry into an intervertebral disc, the intervertebral disc having a nucleus pulposus surrounded by an annulus fibrosis;
    removing the nucleus pulposus from within the intervertebral disc through the point of entry, leaving the intervertebral space for expansion of the scaffolding system of claim 1 within the annulus fibrosis, the intervertebral space having a top vertebral plate and a bottom vertebral plate;
    inserting the expanding frame in the collapsed state through the point of entry into the intervertebral space;
    inserting the central beam into the frame to form the scaffolding system;
    and,
    adding a grafting material to the intervertebral space.

8. The method of claim 7, wherein the connector elements are struts are adapted to stack in the collapsed state to minimize void space for a low profile entry of the frame into the intervertebral space.

9. The method of claim 7, wherein the expanding includes
    expanding the expanding frame laterally to a width that exceeds the width of the point of entry; and,
    inserting the central beam to expand the expanding frame vertically to support the frame in the expanded state.

10. A kit, comprising:
    the scaffolding system of claim 1;
    a cannula for inserting the scaffolding system into the intervertebral space;
    a guidewire adapted for guiding the central beam into the expanding frame; and,
    an expansion handle for inserting the central beam into the expanding frame to form the scaffolding system.

11. The kit of claim 10, the distal end of the frame having a slidably translational connection with the guide that restricts the top beam and the bottom beam to movement relative to the guide when converting the frame from the collapsed state to the expanded state in vivo.

12. The kit of claim 10; wherein, the struts are configured monolithically integral to the first top beam and the first bottom beam, the second top beam and the second bottom beam, the first top beam and the second top beam, and the first bottom beam and the second bottom beam.

13. An intervertebral scaffolding system, comprising:
    a central beam; and,
    an expanding frame having a collapsed state and an expanded state, the frame configured for operably contacting the central beam to create an intervertebral scaffolding system in vivo, the frame having
        a first top beam, a first bottom beam, a second top beam, and a second bottom beam; wherein, the first top beam and the first bottom beam form an angle $\ominus_{FS}$, the second top beam and the second bottom beam form an angle $\ominus_{SS}$, and each of $\ominus_{FS}$ and $\ominus_{SS}$ are independently selected as something other than 0°, such that (i) the first top beam and the first bottom beam or (ii) the second top beam and the second bottom beam, are not substantially parallel in the expanded state;

a plurality of connector elements configured to connect the first top beam to the second top beam, the first bottom beam to the second bottom beam, the first top beam to the first bottom beam, and the second top beam to the second bottom beam, the connecting forming a square, cylindrical shape for engaging with the central beam in vivo to support the expanding frame in the expanded state; and, a guide that restricts the movement of the first top beam relative to the first bottom beam, the second top beam relative to the second bottom beam, the first top beam relative to the second beam, and the first bottom beam relative to the second bottom beam during the expanding;

wherein, the connector elements and guide function together to maintain structural stiffness in the expanding frame in vivo to adequately support localized loading in the intervertebral space in which bone tissue puts pressure on the expanding frame.

14. The scaffolding system of claim 13, wherein the connector elements are configured monolithically integral to the first top beam and the first bottom beam, the second top beam and the second bottom beam, the first top beam and the second top beam, and the first bottom beam and the second bottom beam.

15. The scaffolding system of claim 13, wherein, the connector elements are struts configured monolithically integral to the first top beam and the first bottom beam, the second top beam and the second bottom beam, the first top beam and the second top beam, and the first bottom beam and the second bottom beam.

16. The scaffolding system of claim 13, wherein the first top beam, first bottom beam, second top beam, and second bottom beam are each independently configured to be straight or have a select curvature.

17. The scaffolding system of claim 13, the distal end of the frame having a guide that restricts the movement of the first top beam relative to the first bottom beam, the second top beam relative to the second bottom beam, the first top beam relative to the second beam, and the first bottom beam relative to the second bottom beam when converting the frame from the collapsed state to the expanded state in vivo.

18. The scaffolding system of claim 13, the central beam further comprising a graft port.

19. The scaffolding system of claim 13, wherein $\ominus_{FS}$ and $\ominus_{SS}$ are each independently selected to range from about 0.5° to 31.5°.

20. The scaffolding system of claim 13, wherein $\ominus_{FS}$ and $\ominus_{SS}$ are each independently selected to be about 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, or any angle therein in increments of 0.1°.

* * * * *